(12) United States Patent
Kobayashi et al.

(10) Patent No.: US 10,265,268 B2
(45) Date of Patent: Apr. 23, 2019

(54) EXTERNAL COMPOSITION FOR SCREEN FOAMERS

(71) Applicant: POLA PHARMA INC., Tokyo (JP)

(72) Inventors: Hirokazu Kobayashi, Kanagawa (JP); Takaaki Masuda, Kanagawa (JP); Tetsuya Endo, Kanagawa (JP); Kahori Fujii, Kanagawa (JP)

(73) Assignee: POLA PHARMA INC., Tokyo (JP)

( * ) Notice: Subject to any disclaimer, the term of this patent is extended or adjusted under 35 U.S.C. 154(b) by 0 days.

(21) Appl. No.: 15/539,544

(22) PCT Filed: Dec. 24, 2015

(86) PCT No.: PCT/JP2015/086147
§ 371 (c)(1),
(2) Date: Jun. 23, 2017

(87) PCT Pub. No.: WO2016/104661
PCT Pub. Date: Jun. 30, 2016

(65) Prior Publication Data
US 2017/0354598 A1  Dec. 14, 2017

(30) Foreign Application Priority Data

| Dec. 24, 2014 | (JP) | 2014-267230 |
|---|---|---|
| Dec. 24, 2014 | (JP) | 2014-267231 |
| Dec. 24, 2014 | (JP) | 2014-267232 |
| Dec. 24, 2014 | (JP) | 2014-267233 |
| Dec. 24, 2014 | (JP) | 2014-267234 |
| Dec. 24, 2014 | (JP) | 2014-267235 |
| Dec. 24, 2014 | (JP) | 2014-267236 |
| Dec. 24, 2014 | (JP) | 2014-267237 |
| Dec. 24, 2014 | (JP) | 2014-267238 |
| Dec. 24, 2014 | (JP) | 2014-267239 |
| Dec. 24, 2014 | (JP) | 2014-267240 |
| Dec. 24, 2014 | (JP) | 2014-267241 |
| Dec. 24, 2014 | (JP) | 2014-267242 |
| Dec. 24, 2014 | (JP) | 2014-267243 |
| Dec. 24, 2014 | (JP) | 2014-267244 |
| Dec. 24, 2014 | (JP) | 2014-267245 |
| Dec. 24, 2014 | (JP) | 2014-267246 |
| Dec. 24, 2014 | (JP) | 2014-267247 |
| Dec. 24, 2014 | (JP) | 2014-267248 |
| Dec. 24, 2014 | (JP) | 2014-267249 |
| Dec. 25, 2014 | (JP) | 2014-267271 |
| Dec. 25, 2014 | (JP) | 2014-267272 |
| Dec. 25, 2014 | (JP) | 2014-267273 |
| Dec. 25, 2014 | (JP) | 2014-267274 |
| Dec. 25, 2014 | (JP) | 2014-267275 |
| Dec. 25, 2014 | (JP) | 2014-267276 |
| Dec. 25, 2014 | (JP) | 2014-267277 |
| Dec. 25, 2014 | (JP) | 2014-267278 |
| Dec. 25, 2014 | (JP) | 2014-267279 |
| Dec. 25, 2014 | (JP) | 2014-267280 |
| Dec. 25, 2014 | (JP) | 2014-267281 |

(51) Int. Cl.

| A61K 8/00 | (2006.01) |
|---|---|
| A61K 9/12 | (2006.01) |
| A61K 8/39 | (2006.01) |
| A61Q 19/00 | (2006.01) |
| A61K 8/86 | (2006.01) |
| A61K 8/04 | (2006.01) |
| A61K 31/167 | (2006.01) |
| A61K 31/192 | (2006.01) |

(Continued)

(52) U.S. Cl.
CPC ............... *A61K 9/122* (2013.01); *A61K 8/00* (2013.01); *A61K 8/046* (2013.01); *A61K 8/39* (2013.01); *A61K 8/86* (2013.01); *A61K 31/167* (2013.01); *A61K 31/192* (2013.01); *A61K 31/355* (2013.01); *A61K 31/496* (2013.01); *A61K 31/56* (2013.01); *A61K 31/727* (2013.01); *A61K 47/10* (2013.01); *A61K 47/14* (2013.01); *A61K 47/22* (2013.01); *A61K 47/34* (2013.01); *A61Q 19/00* (2013.01)

(58) Field of Classification Search
None
See application file for complete search history.

(56) References Cited

U.S. PATENT DOCUMENTS 6,231,844 B1   5/2001  Takanori
9,622,947 B2 *  4/2017  Tamarkin ............... A61K 47/10

(Continued)

FOREIGN PATENT DOCUMENTS

EP    1609464 A1   12/2005
JP    08-291050 A  11/1996

(Continued)

OTHER PUBLICATIONS

International Search Report and Written Opinion, International Patent Application No. PCT/JP2015/086147, dated Feb. 23, 2016 with English translation (29 pages).

(Continued)

*Primary Examiner* — Susan T Tran
(74) *Attorney, Agent, or Firm* — Hamre, Schumann, Mueller & Larson, P.C.

(57) ABSTRACT

The present invention addresses the issue of providing an external composition for screen foamers such as pump foamers, that can be safely used even when not removed after application. Provided is an external composition for screen foamers, including a non-ionic surfactant as a foaming component and, ideally, being in a soluble state.

14 Claims, 15 Drawing Sheets

(51) Int. Cl.

| | | |
|---|---|---|
| A61K 31/355 | (2006.01) | |
| A61K 31/496 | (2006.01) | |
| A61K 31/56 | (2006.01) | |
| A61K 31/727 | (2006.01) | |
| A61K 47/10 | (2017.01) | |
| A61K 47/14 | (2017.01) | |
| A61K 47/22 | (2006.01) | |
| A61K 47/34 | (2017.01) | |

(56) References Cited

U.S. PATENT DOCUMENTS

| | | |
|---|---|---|
| 2004/0241099 A1 | 12/2004 | Popp et al. |
| 2011/0059117 A1 | 3/2011 | Seigfried |
| 2013/0164226 A1* | 6/2013 | Nakamoto ............. A61K 9/122 424/43 |

FOREIGN PATENT DOCUMENTS

| | | |
|---|---|---|
| JP | 2002-012513 A | 1/2002 |
| JP | 2002-087942 A | 3/2002 |
| JP | 2003-129097 A | 5/2003 |
| JP | 2003-268400 A | 9/2003 |
| JP | 2003-277230 A | 10/2003 |
| JP | 2004-035458 A | 2/2004 |
| JP | 2006-347896 A | 12/2006 |
| JP | 2007-500235 A | 1/2007 |
| JP | 2007-112746 A | 5/2007 |
| JP | 2007-137813 A | 6/2007 |
| JP | 2012-214422 A | 11/2012 |
| JP | 2013-500239 A | 1/2013 |
| JP | 2014-101333 A | 6/2014 |
| JP | 2014-125436 A | 7/2014 |
| JP | 2015-034162 A | 2/2015 |
| JP | 2015-124179 A | 7/2015 |
| JP | 2015-157804 A | 9/2015 |
| JP | 2015-157805 A | 9/2015 |
| JP | 2015-168654 A | 9/2015 |
| JP | 2015-203029 A | 11/2015 |
| WO | 2004/105702 | 12/2004 |
| WO | 2015/005419 | 1/2015 |

OTHER PUBLICATIONS

Extended European Search Report; European Patent Application No. 15873229.7, dated Jun. 25, 2018 (10 pages).

\* cited by examiner

EXTERNAL COMPOSITION FOR SCREEN FOAMERS

TECHNICAL FIELD

The present invention relates to an external composition for screen foamers which is suitable for external skin preparations, and also relates to an external skin preparation comprising the above composition packed in a screen foamer container.

BACKGROUND ART

Foamable external compositions cause less stress on skin upon application, and can be uniformly applied over a wide area. Therefore, they are widely used in cosmetics and pharmaceutical products (see Patent Documents 1 and 2). However, use of liquefied gases such as LPG and fluoroalkane, which had been predominantly used with foamable external compositions, is now restricted due to the ozone hole problem and others. In addition, there is a concern about irritation due to the gas dissolved in the foam. For these reasons, liquefied gases are now becoming less practical. Accordingly, no-gas formulations with which pump foamers are used are emerging to replace the conventional products (for example, see Patent Documents 3 and 4).

Compositions for pump foamers have been under extensive studies in the field of cleaning agents and the like. According to these studies, combined uses of a nonionic surfactant with mainly an anionic surfactant and an amphoteric surfactant which are excellent in foaming and foam stability are widely explored (see Patent Document 5). However, irritability to mucous membrane and skin becomes an issue when an anionic surfactant and an amphoteric surfactant such as fatty acid soaps having high surface activity effects are formulated. On the other hand, use of a nonionic surfactant, which has a low skin irritability, can not provide sufficient foaming, foam stability, and foam quality may not be obtained due to its low foamability (see Patent Document 6). Further, the aforementioned irritability to mucous membrane and skin is a more serious issue for a cosmetic or medical composition for pump foamers which is used without being washed-off. This is because a component responsible for skin irritation may not be removed by washing. For these reasons, there have been demands for developing a safe composition for screen foamers such as a composition for pump foamers. That is, a foaming means with less irritability for an external composition for screen foamers has been desired.

However, an external composition for screen foamers comprising a less irritating nonionic surfactant as a foaming component has not yet been known, and any attempt has not been tried to formulate such a composition in view of the low formability of nonionic surfactants.

CITATION LIST

Patent Documents

Patent Document 1: Japanese Patent Application Laid-Open No. 2007-112746
Patent Document 2: Japanese Patent Application Laid-Open No. 2006-347896
Patent Document 3: Japanese Patent Application Laid-Open No. 2003-277230
Patent Document 4: Japanese Patent Application Laid-Open No. 2003-129097
Patent Document 5: Japanese Patent Application Laid-Open No. 2002-087942
Patent Document 6: Japanese Patent Application Laid-Open No. 2007-137813

SUMMARY OF INVENTION

Technical Problem

The present invention is made under these circumstances. An object of the present invention is to provide an external composition for screen foamers which can be safely used without being removed after application.

Preferably, another object of the present invention is to provide a technology for forming a good foam with the above external composition. Preferably, yet another object of the present invention is to provide an external composition for screen foamers, having reduced skin irritability when applied or spread, and creating a good foam when discharged even in a case where the content of alcohol is high. Further, another object of the present invention is to provide an external composition for screen foamers capable of: preferably solubilizing an active ingredient for stable blending; increasing the holding amount of the active ingredient; and having an excellent formulation stability after application. Moreover, another object of the present invention is to provide an external composition for screen foamers suitable for treating skin diseases preferably such as atopic dermatitis.

Solution to Problem

After conducting extensive studies to obtain a safe external composition for screen foamers in view of the above circumstances, the present inventors find that an external composition for screen foamers showing the aforementioned effects can be obtained by preferably preparing a composition in a solubilized state using a nonionic surfactant as a foaming component. Then the present invention has been completed. That is, the present invention can provide the followings.

(1) An external composition for screen foamers, comprising a nonionic surfactant as a foaming component.
(2) The external composition according to (1), which is in a solubilized state.
(3) The external composition according to (1) or (2), wherein the total sum of the content of the ionic surfactant is 1 mass % or less.
(4) The external composition according to any one of (1) to (3), which is intended for use without being removed after application.
(5) The external composition according to any one of (1) to (4), which is an aqueous system.
(6) The external composition according to any one of (1) to (5), wherein the nonionic surfactant has an HLB value of 9 or more.
(7) The external composition according to any one of (1) to (6), wherein the nonionic surfactant comprises one or more surfactants selected from the group A below:
(Group A)
polyoxyethylene alkyl ether, polyoxyethylene alkenyl ether, polyoxyethylene hydrogenated castor oil, polyoxyethylene fatty acid ester, polyoxyethylene sorbitan fatty acid ester, polyoxyethylene fatty acid glyceryl, polyoxypropylene polyoxyethylene alkyl ether, and polyoxypropylene polyoxyethylene alkenyl ether.

(8) The external composition according to (7), wherein the proportion of the nonionic surfactants selected from the group A accounts for 80 mass % or more of the total amount of the nonionic surfactant contained in the external composition.

(9) The external composition according to (7) or (8), wherein a carbon chain of a hydrophobic group in a nonionic surfactant of the group A has a carbon number of 8 or more.

(10) The external composition according to any one of (1) to (9), comprising 10 mass % or more of alcohol in total.

(11) The external composition according to any one of (1) to (10), comprising phospholipid.

(12) The external composition according to any one of (1) to (11), comprising 1 to 40 mass % of one or more selected from the group of solvents shown below:

(Solvent) N-alkyl pyrrolidone, alkylene carbonate, benzyl alcohol, adipic acid diester, sebacic acid diester.

(13) The external composition according to (12), comprising a poorly water-soluble or lipophilic active ingredient.

(14) An external composition, comprising 1 to 15 mass % of one or more nonionic surfactants selected from the group A below; and 0.001 to 10 mass % of a steroid, a non-steroid antiinflammatory agent, a microbicide, an antifungal agent, an antibiotic, an anti-itching agent, vitamin A, vitamin B, vitamin C, vitamin D, vitamin E, and an immunosuppressive agent, a mucopolysaccharide such as hyaluronic acid and a heparinoid, and the like as active ingredients, wherein the external composition is in a solubilized state:

(Group A)
polyoxyethylene alkyl ether, polyoxyethylene alkenyl ether, polyoxyethylene hydrogenated castor oil, polyoxyethylene fatty acid ester, polyoxyethylene sorbitan fatty acid ester, polyoxyethylene fatty acid glyceryl, polyoxypropylene polyoxyethylene alkyl ether, and polyoxypropylene polyoxyethylene alkenyl ether.

(15) An external skin preparation, comprising the external composition according to any one of (1) to (14) packed in a screen foamer container.

(16) A method of designing an aqueous external composition for screen foamers, comprising: selecting one or more nonionic surfactants from the group A within the range of 1 to 15 mass % in total; and selecting one or more alcohols from the group B within the content range of 5 to 55 mass % in total, wherein a composition prepared by heating and cooling constituent components with stirring is in a solubilized state:

(Group A)
polyoxyethylene alkyl ether, polyoxyethylene alkenyl ether, polyoxyethylene hydrogenated castor oil, polyoxyethylene fatty acid ester, polyoxyethylene sorbitan fatty acid ester, polyoxyethylene fatty acid glyceryl, polyoxypropylene polyoxyethylene alkyl ether, and polyoxypropylene polyoxyethylene alkenyl ether.

(Group B)
ethanol, isopropyl alcohol, propylene glycol, dipropylene glycol, glycerin, diglycerin, 1,3-butylene glycol, 1,2-pentanediol, 1,2-hexanediol, polyethylene glycol, and polypropylene glycol.

Advantageous Effect of Invention

The present invention can provide an external composition for screen foamers, which can be used safely without being removed immediately after application. A preferred embodiment of the present invention can provide an external composition for screen foamers, which can create a good foam.

Another preferred embodiment of the present invention can provide an external composition for screen foamers having reduced skin irritability when applied or spread, which can be used safely without being washed off. Further, the composition according to a preferred embodiment of the present invention can solubilize an active ingredient for stable blending, and have a high holding amount of the active ingredient, and have an excellent formulation stability after application. Moreover, according to a preferred embodiment of the present composition, the foamability after discharge is satisfactory, and the foam is fine, uniform, soft, and highly elastic, and the foam easily disappears and is dried without leaving a foaming trace within an appropriate time period after application, and the application uniformity of an active ingredient and spreadability upon application are excellent. A preferred embodiment of the present invention can provide a composition for screen foamers, which is suitable for treating skin diseases such as atopic dermatitis.

According to the present invention, an external composition for screen foamers which can be safely used without being removed immediately after application can easily be designed.

BRIEF DESCRIPTION OF DRAWINGS

FIG. 15 shows images illustrating the results from Example 34.

Figure 1:
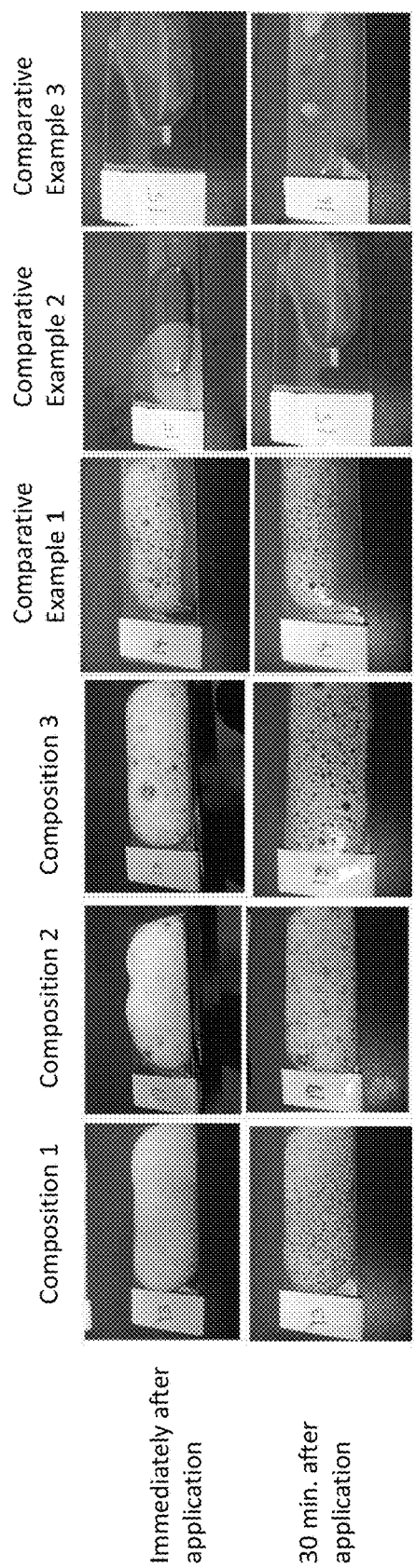
FIG. 1 shows images illustrating the results from Example 1.

DESCRIPTION OF EMBODIMENT (1) Nonionic Surfactant as an Essential Constituent of the Composition According to the Present Invention The composition according to the present invention can be characterized by comprising a nonionic surfactant as a foaming component. The above component can allow a foam to be aligned on a gas-liquid interface to reduce the surface tension of the gas-liquid interface, improving the foamability of the foam, the stability of the foam formed, the uniformity and spreadability when applied.

There is no particular limitation for the nonionic surfactant used in the composition according to the present invention as long as it is a nonionic surfactant which can be formulated with an external skin preparation.

Further, the HLB value of the nonionic surfactant is preferably 9 or more, more preferably 10 or more, even more preferably 11 or more, and in particular preferably 13 or more. The HLB value of the nonionic surfactant is, for example, 10 to 19.

For the nonionic surfactant, one or more selected from the group A below are preferably used:
(Group A)
polyoxyethylene alkyl ether, polyoxyethylene alkenyl ether, polyoxyethylene hydrogenated castor oil, polyoxyethylene fatty acid ester, polyoxyethylene sorbitan fatty acid ester, polyoxyethylene fatty acid glyceryl, polyoxypropylene polyoxyethylene alkyl ether, and polyoxypropylene polyoxyethylene alkenyl ether.

Among these, an embodiment is preferred in which the nonionic surfactant comprises polyoxyethylene alkyl ether and/or polyoxyethylene alkenyl ether. Preferred embodiments of the present invention can include, for example, an embodiment in which the nonionic surfactant comprises only polyoxyethylene alkyl ether and/or polyoxyethylene alkenyl ether; and an embodiment in which one or more selected from polyoxyethylene fatty acid ester, polyoxyethylene sorbitan fatty acid ester, and polyoxyethylene hydrogenated castor oil are combined in addition to polyoxyethylene alkyl ether and/or polyoxyethylene alkenyl ether. Further, as components to be combined with polyoxyethylene alkyl ether and/or polyoxyethylene alkenyl ether, polyoxyethylene fatty acid ester and/or polyoxyethylene hydrogenated castor oil are particularly preferred, and the combination of the both can also be preferably mentioned. Moreover, an embodiment in which only polyoxyethylene sorbitan fatty acid ester is used as the nonionic surfactant can also be preferably mentioned.

The nonionic surfactant is preferably blended in the composition according to the present invention in an amount required for bringing the composition into a solubilized state.

For example, the nonionic surfactant is preferably included in an amount of 1 to 15 mass % relative to the entire composition. Further, the nonionic surfactant is preferably included in an amount of 2 to 12 mass %, more preferably 2 to 10 mass %, even more preferably 2.5 to 10 mass %, and in particular preferably 2.5 to 7 mass % relative to the entire composition.

The proportion of the nonionic surfactant having the above predetermined HLB value preferably accounts for 80 mass % or more, more preferably 90 mass % or more, and in particular preferably 95 mass % or more relative to the total amount of the nonionic surfactant. For example, the nonionic surfactant having an HLB value of 9 or more, preferably 10 or more, even more preferably 11 or more, and in particular preferably 13 or more may preferably account for the entire amount of the nonionic surfactant.

The proportion of the one or more surfactants selected from the group A preferably accounts for 80 mass % or more, more preferably 90 mass % or more, and in particular preferably 95 mass % or more of the total amount of the nonionic surfactant. For example, the one or more surfactants selected from the group A may preferably account for the entire amount of the nonionic surfactant.

Further, the proportion of polyoxyethylene alkyl ether and/or polyoxyethylene alkenyl ether is preferably 25 mass % or more, more preferably 40 mass % or more, and even more preferably 50 mass % or more relative to the total amount of the nonionic surfactant. There is no particular limitation for the upper limit of the proportion, including 90 mass % or less, preferably 80 mass % or less.

In a case where other nonionic surfactants are included as the nonionic surfactant in addition to polyoxyethylene alkyl ether and/or polyoxyethylene alkenyl ether, the total content of polyoxyethylene alkyl ether and/or polyoxyethylene alkenyl ether relative to the total content of the nonionic surfactants other than polyoxyethylene alkyl ether and/or polyoxyethylene alkenyl ether is preferably 1:5 to 5:1 by mass ratio, more preferably 1:4 to 4:1, even more preferably 1:3 to 3:1.

A carbon chain of a hydrophobic group in the nonionic surfactant preferably has a carbon number of 8 or more, more preferably 10 or more, and in particular preferably 12 or more. Further, the upper limit of the carbon number is preferably 24, more preferably 22.

The carbon number of alkyl or alkenyl in polyoxyethylene alkyl ether or polyoxyethylene alkenyl ether is preferably 10 to 24, more preferably 12 to 22.

Preferred examples of polyoxyethylene alkyl ether or polyoxyethylene alkenyl ether can include polyoxyethylene oleyl ether, polyoxyethylene stearyl ether, polyoxyethylene lauryl ether, polyoxyethylene cetyl ether, polyoxyethylene behenyl ether, and the like.

Further the average addition mole number of polyoxyethylene is preferably 2 to 50, more preferably 4 to 45, even more preferably 4 to 40, and in particular preferably 6 to 30.

The fatty acid in polyoxyethylene fatty acid ester preferably has a carbon number of 8 to 24, more preferably 12 to 18.

Preferred examples of polyoxyethylene fatty acid ester can include saturated, unsaturated fatty acid esters of polyoxyethylene such as polyoxyethylene oleate (polyethylene glycol oleate), polyoxyethylene stearate (polyethylene glycol stearate), and polyoxyethylene laurate (polyethylene glycol laurate). In particular, preferred examples can include polyoxyethylene monooleate (polyethylene glycol monooleate), polyoxyethylene monostearate (polyethylene glycol monostearate), and polyoxyethylene monolaurate (polyethylene glycol monolaurate).

Further, the average addition mole number of polyoxyethylene is preferably 5 to 70, more preferably 5 to 65, and even more preferably 5 to 55.

The fatty acid in polyoxyethylene sorbitan fatty acid ester preferably has a carbon number of 12 to 18. Suitable examples of polyoxyethylene sorbitan fatty acid ester can include polyoxyethylene sorbitan monolaurate, polyoxyethylene sorbitan monopalmitate, polyoxyethylene sorbitan monooleate, polyoxyethylene sorbitan monostearate, polyoxyethylene sorbitan trioleate, polyoxyethylene sorbitan tetraoleate, and the like.

Further, the average addition mole number of polyoxyethylene is preferably 5 to 50, more preferably 10 to 25.

Suitable examples of polyoxyethylene hydrogenated castor oil can include those having an average addition mole number of polyoxyethylene of 20 to 100.

The fatty acid in polyoxyethylene fatty acid glyceryl preferably has a carbon number of 8 to 24, more preferably 12 to 18. Suitable examples of polyoxyethylene fatty acid glyceryl can include polyethylene glycol monostearate, polyethylene glycol monooleate and the like.

Further, the average addition mole number of polyoxyethylene is preferably 10 to 55, more preferably 10 to 45.

The alkyl or alkenyl in polyoxypropylene polyoxyethylene alkyl ether or polyoxypropylene polyoxyethylene alkenyl ether preferably has a carbon number of 16 to 24.

Preferred examples of polyoxypropylene polyoxyethylene alkyl ether or polyoxypropylene polyoxyethylene alkenyl ether can include polyoxypropylene polyoxyethylene cetyl ether and the like.

Further, the average addition mole number of polyoxyethylene is preferably 1 to 30, more preferably 10 to 20. Moreover, the average addition mole number of polyoxypropylene is preferably 4 to 8.

The composition according to the present invention may further comprise a nonionic surfactant having an HLB value of 5 or less, in addition to the nonionic surfactant having an HLB value of 9 or more. There is no particular limitation for the nonionic surfactant having an HLB value of 5 or less according to the present invention as long as it can be formulated in an external skin preparation and the like. Suitable examples of the above nonionic surfactant can include glycerin fatty acid ester, sorbitan fatty acid ester, and the like. Suitable examples of the above glycerin fatty acid ester can include, for example, glyceryl monostearate and glyceryl monomyristate. Suitable examples of the above sorbitan fatty acid ester can include sorbitan monostearate (HLB 4.7), sorbitan monooleate (HLB 4.3), sorbitan tristearate (HLB 2.1), sorbitan trioleate (HLB 1.7), sorbitan sesquistearate (HLB 4.2), sorbitan sesquioleate (HLB 3.7), and the like. Glyceryl monostearate and sorbitan monostearate are preferably mentioned. The nonionic surfactant having an HLB value of 5 or less according to the present invention may be included in an amount of 0.1 to 10 mass %, more preferably 1 to 5 mass % relative to the entire composition. Further, the ratio of 1:3 to 3:1, more preferably 1:2 to 2:1 can preferably be mentioned relative to the total content of the nonionic surfactant having an HLB value of 9 or more, preferably 10 or more, more preferably 11 or more, in particular preferably 13 or more, and for example, 10 to 19.

Examples of the combination of the nonionic surfactant having an HLB value of 9 or more and the nonionic surfactant having an HLB value of 5 or less can include, as nonionic surfactants, a combination of polyoxyethylene alkyl ether and/or polyoxyethylene alkenyl ether having an HLB value of 9 or more and glyceryl monostearate and/or sorbitan monostearate having an HLB value of 5 or less; and a combination of one or more selected from polyoxyethylene fatty acid ester, polyoxyethylenized sorbitan fatty acid ester, and optionally-polyoxyethylenized castor oil, and glyceryl monostearate and/or sorbitan monostearate having an HLB value of 5 or less in addition to polyoxyethylene alkyl ether and/or polyoxyethylene alkenyl ether having an HLB value of 9 or more. Further, when a nonionic surfactant having an HLB value of 9 or more and a nonionic surfactant having an HLB value of 5 or less are blended together, the weighted average is preferably 9 to 16.

An aliphatic alkanolamide-based surfactant can also be used as a nonionic surfactant.

There is no particular limitation for the aliphatic alkanolamide-based surfactant as long as it can be used in common external skin preparations such as external medicaments and cosmetics. Specifically preferred examples can include coconut oil fatty acid monoethanolamide (Cocamide MEA), coconut oil fatty acid diethanolamide (Cocamide DEA), Lauric acid monoethanolamide (Lauramide MEA), Lauric acid diethanolamide (Lauramide DEA), Lauric acid monoisopropanolamide (Lauramide MIPA), Palmitic acid monoethanolamide (Palmitamide MEA), Palmitic acid diethanolamide (Palmitamide DEA), Coconut oil fatty acid methylethanolamide (Cocamide methyl MEA), and the like. Coconut oil fatty acid diethanolamide, lauric acid diethanolamide, and palmitic acid diethanolamide can be preferably mentioned. One or more selected from these components can be included in the composition. The content of the aliphatic alkanolamide-based surfactant is, for example, 0.5 to 10 mass %, for example, 1 to 5 mass %.

(2) Composition According to the Present Invention

The composition according to the present invention is a composition for screen foamers. As used herein, the screen foamer means a structure having a mechanism for mixing a liquid with air to effect foaming by pressurizing the liquid to pass through a mesh-like screen. Pump foamers, tube foamers, and the like are known, and in particular pump foamers can be preferably mentioned. A pump foamer has a mechanism for discharging a content in a foamy form, the content being pumped with a pump.

The composition according to the present invention comprises the aforementioned essential constituent as a foaming component. That is, the nonionic surfactant in the composition according to the present invention functions as a foaming component to achieve foaming with a screen foamer such as a pump foamer.

The composition according to the present invention is preferably in a solubilized state.

The solubilized state refers to a state where a surfactant forms micells, and materials insoluble in a solvent is transparently and uniformly dissolved to form a single phase solution. Examples of the solubilized state include a microemulsion state. Microemulsion, which comprises emulsified particles with a fine particle diameter of 100 nm or less, is a thermodynamically stable micellar solution. A system may be considered to be in a solubilized state if its appearance is transparent. Alternatively, a solubilized state may be determined by measuring a particle size by the conventional method.

Good foamability can be obtained by achieving a solubilized state. Further, the strength of foam after foaming can be improved by achieving such a state. Moreover, in such a state, crystals and the like are not formed, and the stability after long-term storage is improved.

The composition according to the present invention is preferably in a form of an external skin composition such as an external medicament for skin and cosmetics. In particular the composition according to the present invention is intended for use without being removed after application.

The composition according to the present invention is preferably an aqueous system. The aqueous system as used herein means that water is contained to the extent where water can serve as a base material. The content of water, for example, is 15 mass % or more, preferably 20 mass % or more, and more preferably 30 mass % or more.

The composition according to the present invention is characterized by comprising 40 to 85 mass % of water, more preferably 50 to 80 mass %, and even more preferably 55 to 75 mass %. Water, which is an important component of the foam interface for forming foam when discharged with a pump foamer in the present invention, has good foamability and excellent foam persistency if in the above range. Water contained in an amount within the above range is effective for stably maintaining foam during application when used for external use.

(3) Optional Components

The composition according to the present invention may comprise any component used in external compositions such as external medicaments for skin and cosmetics, in addition to the aforementioned essential constituent. Preferred examples of the optional component can include, for example, hydrocarbons such as liquid paraffin and squalane; esters such as jojoba oil, oleyl ester of dodecanoic acid, and cetyl isooctanate; N-alkyl pyrrolidones such as N-methyl-2-pyrrolidone and N-ethyl-2-pyrrolidone; alkylene carbonates with a carbon number of 2 to 4 such as ethylene carbonate and propylene carbonate; diesters of dibasic acid with a carbon number of 5 to 12 such as crotamiton, triethyl citrate, ethyl ether of diethylene glycol, triacetin, diisopropyl adipate, diethyl adipate, and diisopropyl sebacate; solvents such as benzyl alcohol, acetone, methyl ethyl ketone, and ethylene glycol alkyl ether; polyhydric alcohols such as propylene glycol, 1,3-butylene glycol, glycerin, dipropylene glycol, diglycerin, polyethylene glycol, maltitol, and sorbitol; monohydric alcohols such as ethanol, isopropanol, oleyl alcohol, and isostearyl alcohol; fatty acids such as oleic acid and isostearic acid; thickening agents such as carboxyvinyl polymer and xanthan gum; microbicides such as paraben and chlorhexidine gluconate. A suitable substance can be appropriately selected from these optional components to be included. The preferred contents of these components may vary depending on their formulation purposes, but the contents are generally about 0.1 to 20 mass %.

The composition according to the present invention preferably comprises a solvent selected from the followings: (Solvent) N-alkyl pyrrolidone, alkylene carbonate, benzyl alcohol, adipic acid diester, sebacic acid diester.

These solvents, which have an excellent solubilizing power to solubilize poorly soluble pharmaceutical agents, can solubilize a poorly soluble pharmaceutical agent such that it may be stably contained in a composition.

Preferred examples of N-alkyl pyrrolidone can include N-alkyl-2-pyrrolidone having an alkyl chain with a carbon number of 1 to 4. In particular, N-methyl-2-pyrrolidone and N-ethyl-2-pyrrolidone are preferred.

As alkylene carbonate, propylene carbonate is preferred.

Examples of adipic acid diester can include diethyl adipate and diisopropyl adipate.

Examples of sebacic acid diester can include diethyl sebacate and diisopropyl sebacate.

Further, acetone, methyl ethyl ketone, and ethylene glycol alkyl ether may also be mentioned as a solvent.

These components may be included alone in a composition. Alternatively one or more of them may be selected to be included in a composition. Further, the preferred content of a solvent in the composition according to the present invention is preferably 1 to 40 mass % relative to the entire composition, more preferably 1 to 30 mass %, even more preferably 1 to 15 mass %, in particular preferably 1 to 10 mass %, and more preferably 3 to 8 mass %. Further, a solvent is contained in an amount of 20 to 5000 times by mass of a poorly soluble pharmaceutical agent (an active ingredient), more preferably 30 to 2500 times by mass, and even more preferably 40 to 1000 times by mass. Examples of the content can include, for example, 20 to 250 times by mass and more preferably 30 to 200 times by mass. This component can enhance the strength of a discharged foam. Moreover, a poorly soluble pharmaceutical agent (an active ingredient) can be stably blended when it is included. Furthermore, this component can reduce a feeling of irritation during application and spreading. The aforementioned contents are preferred in order to obtain these effects.

The composition according to the present invention preferably comprises alcohol. Alcohol as used in the present invention collectively refers to monohydric alcohol and polyhydric alcohol. Such alcohol is preferably miscible with water at any ratio.

Examples of monohydric alcohol can include, for example, ethanol, isopropyl alcohol and the like.

Preferred examples of polyhydric alcohol can include, for example, propylene glycol, dipropylene glycol, glycerin, diglycerin, 1,3-butylene glycol, 1,2-pentanediol, 1,2-hexanediol, polyethylene glycol, polypropylene glycol, and the like. As particularly preferred polyhydric alcohols among these, one or more selected from 1,3-butylene glycol, polyethylene glycol, glycerin, and propylene glycol are preferred. In particular, polyethylene glycol and 1,3-butylene glycol can suitably be mentioned. Further, the molecular weight of a polyhydric alcohol as used in the present invention is preferably 3500, more preferably 2000 or less.

With regard to the total content of the aforementioned alcohol, the lower limit is preferably 10 mass %, more preferably 12 mass %, and in particular preferably 15 mass %. The upper limit is preferably 55 mass %, more preferably 45 mass %, in particular preferably 40 mass %, and for example, 30 mass %.

The content of monohydric alcohol is preferably 5 to 25 mass %, more preferably 5 to 20 mass %, even more preferably 5 to 15 mass %.

The content of polyhydric alcohol is preferably 10 to 55 mass %, more preferably 12 to 45 mass %, in particular preferably 15 to 40 mass %, and for example, 15 to 30 mass %.

For example, the preferred content of alcohol including monovalent alcohol and polyhydric alcohol is preferably 5 to 55 mass % relative to the entire composition, more preferably 10 to 55 mass %, even more preferably 12 to 45 mass %, and further preferably 15 to 30 mass %. In addition, polyhydric alcohol as the aforementioned alcohol is preferably included in an amount of 10 mass % or more relative to the entire composition, preferably 10 to 55 mass %, more preferably 12 to 45 mass %, and in particular preferably 15 to 30 mass %. A discharged foam can be maintained for a long time when the aforementioned approaches are used. Further, impression from use, such as a feeling of moisturization can be improved.

Preferred embodiments of the composition according to the present invention can include the followings.

Preferred are an embodiment in which ethanol is contained in an amount of 5 to 20 mass %, more preferably 10 to 15 mass %; an embodiment in which polyhydric alcohol is contained in addition to ethanol; an embodiment in which polyethylene glycol is contained in an amount of 0.5 to 30 mass %, more preferably 1.5 to 25 mass %, in addition to another polyhydric alcohol; an embodiment in which 1,3-butylene glycol is contained in an amount of 5 to 40 mass %, more preferably 5 to 30 mass %, and even more preferably 10 to 25 mass %; an embodiment in which another polyhydric alcohol is also contained in addition to the aforementioned 1,3-butylene glycol.

The aforementioned alcohol, in particular, polyhydric alcohol contained in a high concentration enables formation of an interface-enforced foam by virtue of an interaction with a nonionic surfactant as described below. Further, the inclusion of a high concentration of alcohol can provide a composition with which a feeling of moisturization can be obtained.

The composition according to the present invention preferably comprises phospholipid. There is no particular limitation for the phospholipid as long as it is used in common external skin preparations such as external medicaments and cosmetics. Specifically, suitable examples can include lecithin purified from soybean and egg yolk; phosphatidylcholine, the main component of lecithin; hydroxylated lecithin; phosphatidic acid, the main chain of phosphatidylcholine; hydrogenerated lecithin; phosphatidylserine; phosphatidylinositol; phosphatidylethanolamine; phosphatidylglycerol; sphingomyelin; cerebroside; and the like. Further, lyso-forms thereof can similarly be included. Among these, lecithin and hydrogenation lecithin are preferred.

These components have an effect for improving the foam quality of the composition. Further, these components have excellent moisturizing effects, and enables defoaming in an appropriate time range after application without reducing foamability. This can lead to a low irritability upon application and spreading and good spreadability without leaving any foaming trace. Therefore, they are suitable for application to a skin of such as in atopic dermatitis and the like in which skin barrier functions are decreased. These components may be contained alone, or in a combination of two or more. Phospholipid is included in an amount of 0.001 to 10 mass % relative to the entire composition, more preferably 0.01 to 5 mass %, and in particular preferably 0.01 to 1 mass %. The above components can enhance the strength of a discharged foam, and can prevent denaturation of a foam due to the influence of pH. Moreover, the above components can improve impression from use during application and spreading, and can also avoid skin irritation. In order to obtain these effects, the aforementioned contents are preferred.

In addition to the aforementioned phospholipid, the followings may be included: sebum components such as squalene, cholesterol, cholesterol ester, wax ester, triglyceride, diglyceride, monoglyceride, ceramide, and free fatty acid; amino acids such as serine and glycine; natural moisturizing agents such as pyrrolidonecarboxylic acid and salts thereof, urea, and lactic acid; and acidic mucopolysaccharides such as hyaluronic acid; and the like.

The composition according to the present invention may comprise an organic salt and/or an inorganic salt. The composition according to the present invention is adjusted for the acidity or alkalinity with an organic salt and/or an inorganic salt, and can show excellent foamability, foam stability, and foam quality without affected by the acidity or alkalinity in the range of strong acidity to strong alkalinity (pH 2 to 12). Examples of the organic salt and/or the inorganic salt can include, without limited to these, for example, hydrochloric acid, citric acid, gluconic acid, succinic acid, acetic acid, tartaric acid, sorbic acid, lactic acid, maleic acid, sulfuric acid, phosphoric acid, malic acid, arginine, aqueous ammonia, diisopropanolamine, diethanolamine, triisopropanolamine, triethanolamine, monoethanolamine, potassium hydroxide, calcium hydroxide, and sodium hydroxide, or salts thereof. The specific amount of the organic salt and/or the inorganic salt which may be used in the present invention may vary depending on the organic salt and/the inorganic salt to be used, but it is an amount required for adjusting the acidity or alkalinity of the composition to the above pH range. In general, it is 0.01 to 10 mass % relative to the entire composition, more preferably 0.1 to 5 mass %. The composition according to the present invention may be used as a cleaning agent when it is alkaline, and may be used in pharmaceutical products, cosmetics, and the like with reduced skin irritability when it is weakly acidic. When weakly acidic, it is particularly suitable for use in pharmaceutical products and cosmetics which are used without being removed after application.

The composition according to the present invention may comprise a component selected from aminocarboxylic acid derivatives and salts thereof, phosphonic acid derivatives and salts thereof, phenanthroline derivatives and salts thereof, phytic acid derivatives and salts thereof, gluconic acid derivatives and salts thereof. Preferred examples of the aforementioned amino acid carboxylic acid derivatives and salts thereof can include ethylenediaminetetraacetic acid and salts thereof, nitrilotriacetic acid and salts thereof, diethylenetriaminepentaacetic acid and salts thereof, hydroxyethylethylenediaminetriacetic acid and salts thereof, triethylenetetraminehexaacetic acid, and salts thereof, 1,3-propanediaminetetraacetic acid and salts thereof, 1,3-diamino-2-hydroxypropanetetraacetic acid and salts thereof, hydroxyethyliminodiacetic acid and salts thereof, dihydroxyethyl glycine and salts thereof, glycoletherdiaminetetraacetic acid and salts thereof, dicarboxymethylglutamic acid and salts thereof, (S,S)-ethylenediaminesuccinic acid and salts thereof, and the like. Salts of ethylenediaminetetraacetic acid are preferred. Preferred examples of the aforementioned phosphonic acid derivatives and salts thereof can include hydroxyethylidenediphosphonic acid and salts thereof, nitrilotris (methylene phosphonic acid) and salts thereof, phosphonobutane tricarboxylic acid and salts thereof, ethylenediaminetetra(methylene phosphonic acid) and salts thereof, and the like. Hydroxyethylidenediphosphonic acid and salts thereof are preferred. Preferred examples of the aforementioned phetinic acid derivatives and salts thereof can include phetinic acid and salts thereof. Preferred examples of gluconic acid derivatives and salts thereof can include gluconic acid derivatives. These components are preferably included in an amount of 0.0001 to 10 mass % relative to the entire composition, more preferably 0.001 to 5 mass %. Further, they can prevent decomposition and denaturation of an active ingredient or formulation components to improve formulation stability.

In the composition according to the present invention, use of the following components is preferably restricted in view of safety, in particular to avoid components which may cause irritation or a feeling of irritation in persons with sensitive skin.

The total sum of the content of ionic surfactants except for phospholipid is preferably 1 mass % or less, and preferably, they are not substantially included.

Among nonionic surfactants, use of alkanolamide-based surfactants is also preferably restricted. In a particularly preferred embodiment, they are not substantially included. Among nonionic surfactants, use of polyoxyethylene polyoxypropylene glycol, which may induce anaphylaxis in mucous membrane, is also preferably restricted.

The usage amount of these nonionic surfactants as a proportion against the entire nonionic surfactant is preferably 20 mass % or less, more preferably 10 mass % or less, even more preferably 5 mass % or less, and in particular preferably, they are not included.

Preferably, silicone is also not substantially included.

The composition according to the present invention is preferably in a solubilized state, and can create foam by virtue of nonionic surfactant. Further, according to a preferred embodiment of the present invention, at least one of the followings is excellent: foamability; foam stability; and foam quality such as fineness, softness, and elasticity of foam; impression from use such as a feeling of moisturization; a feeling from use such as application uniformity and spreadability.

An active ingredient is to be included in order to use the composition according to the present invention as a pharmaceutical composition. Preferred examples of the above active ingredient can include, for example, steroids such as hydrocortisone, clobetasone, dexamethasone, and betamethasone, and derivatives thereof; non-steroid antiinflammatory agents such as indomethacin and suprofen; microbicides such as chlorhexidine glyconate and benzalkonium chloride; antifungal agents such as terbinafine, butenafine, bifonazole, and ketoconazole; antibiotics such as penicillin, methicillin, tetracycline, colistinmethanesulfonic acid, and phosphomycin; Anti-itching agents such as nalfurafine; immunosuppressive agents such as vitamin As, vitamin Bs, vitamin Cs, vitamin Ds, vitamin Es, and tacrolimus; mucopolysaccharides such as hyaluronic acid and heparinoids. The contents of these are generally 0.001 to 10 mass %, more preferably 0.01 to 10 mass %, and even more preferably 0.01 to 5 mass %.

For example, a compound selected from betamethasone and derivatives thereof may be included as an active ingredient. Betamethasone is a compound as known under the IUPAC name (8S,9R,10S,11S,13S,14S,16S,17R)-9-fluoro-11,17-dihydroxy-17-(2-hydroxyacetyl)-10,13,16-trimethyl-6,7,8,9,10,11,12,13,14,15,16,17-dodecahydro-3H-cyclopenta[a]phenanthrene-3-one (CAS No. 378-44-9). Further, suitable examples of betamethasone derivatives can include ester derivatives such as phosphoric acid ester, valeric acid ester, butyric acid ester, and propionic acid ester. These esters may be an ester of one acid, or may be an ester of mixed acids. Examples of the composition according to the present invention can include those comprising betamethasone butyrate propionate as an active ingredient. The preferred content in the composition of an active ingredient selected from the aforementioned betamethasone and derivatives thereof is 0.001 to 1 mass %, more preferably 0.005 to 0.5 mass %. A compound selected from betamethasone and derivatives thereof, if contained within the above content range, can be solubilized and formulated into the external skin preparation according to the present invention. Further, a compound selected from betamethasone and derivatives thereof, if contained in the composition according to the present invention within the above content range, can provide therapeutic effects such as anti-inflammatory treatment effects, atopic skin treatment effects, immunosuppression effects.

The composition according to the present invention can provide foams having a wide variety of properties by changing the content of a formulation component and the like. In order to obtain foam properties (the size, uniformity, and hardness of foam) suitable for treating the aforementioned skin diseases, a pump foamer composition having foam properties suitable for a condition of each disease can be appropriately selected for use among the compositions according to the present invention. The above foam properties may be evaluated by visual inspection, or may be evaluated by using physically measurable values. The foam properties may be evaluated using such physically measurable values, including the size of foam in terms of the foam volume, the moving rate of a foam applied on an inclined glass, and the like.

The external composition obtained as described above, which can uniformly solubilize an active ingredient, and can be used in a foamy form during use, can be spread smoothly over an affected area without causing a feeling of irritation to uniformly apply the active ingredient to the affected area. Further, depending on pharmacological effects of an active ingredient, the aforementioned formulation can be suitably used for treatment, i.e., therapy of skin diseases such as skin inflammation, eczema, atopic dermatitis, psoriasis, acne, scarring, and bedsore; prophylactic therapy for preventing aggravation; and prevention of onset.

The composition according to the present invention can be prepared by processing the aforementioned essential constituent and optional components according to the conventional method to preferably achieve a solubilized state.

The composition according to the present invention can improve the strength of a foam after foaming, i.e., foamability when it is preferably in a solubilized state. Further, according to the composition of the present invention, crystals and the like are not precipitated, and the stability after long-term storage is improved. Moreover, the composition according to the present invention can be used in a formulation having a wide range of pH.

(4) External Skin Preparation According to the Present Invention

The external skin preparation according to the present invention is characterized by being packed in a screen foamer container. As used herein, the screen foamer means a structure having a mechanism for mixing a liquid with air to effect foaming by pressurizing the liquid to pass through a mesh-like screen. Pump foamers, tube foamers, and the like are known, and in particular pump foamers can be preferably mentioned. Pump foamers have a mechanism for discharging a content pumped with a pump as a foamy form. The screen foamer container means a container having the above mechanism.

The external skin preparation according to the present invention comprises the composition according to the present invention packed preferably in a pump foamer container. The pump foamer container means a container combined with a container for storing a content to be pumped into the pump foamer. Such a container is already known (see Japanese Patent Application Laid-Open No. 2012-45525 and Japanese Patent Application Laid-Open No. 2008-307478) or commercially available. Therefore, a commercially available product can be appropriately purchased and used. When arranged in the configuration described above, the external composition according to the present invention can be used as a firm foam, and thereby can be uniformly applied without placing a burden on an affected area owing to outstanding spreadability and gentle coatability.

In view of the aforementioned advantages as a foamy dosage form, the external skin preparation according to the present invention is in particular preferably a pharmaceutical product. It may be used without being removed after application when used as a pharmaceutical product. The pharmaceutical product according to the present invention is excellent in safety and foamability.

The present invention also relates to an external composition comprising 1 to 15 mass % of one or more nonionic surfactants selected from the group A; and 0.001 to 10 mass % of a steroid, a non-steroidal antiinflammatory agent, a microbicide, an antifungal agent, an antibiotic, an anti-itching agent, vitamin A, vitamin B, vitamin C, vitamin D, vitamin E, and an immunosuppressive agent as active ingredients, in which the external composition is in a solubilized state. In particular, an embodiment comprising a naphthylamine-based agent, a benzylamine-based agent, an azole-based agent, a dithiolane-based antifungal agent as an antifungal agent is preferably mentioned. Such an external composition is suitable for including an effective amount of an active ingredient. It is also suitable as a forming agent, in particular as a composition for screen foamers. The aforementioned descriptions about preferred components also apply to the embodiment described above.

(5) Design Method According to the Present Invention

The design method according to the present invention comprises selecting a nonionic surfactant selected from the group A as an essential constituent within the range of 1 to 15 mass %.

(Group A)

polyoxyethylene alkyl ether, polyoxyethylene alkenyl ether, polyoxyethylene hydrogenated castor oil, polyoxyethylene fatty acid ester, polyoxyethylene sorbitan fatty acid ester, polyoxyethylene fatty acid glyceryl, polyoxypropylene polyoxyethylene alkyl ether, and polyoxypropylene polyoxyethylene alkenyl ether.

These nonionic surfactants are selected within the range of 1 to 15 mass %.

The preferred aspect and content of a nonionic surfactant are as described above.

The design method according to the present invention comprises selecting an alcohol selected from the group B as an essential constituent in the range of 5 to 55 mass %. Alcohol has an effect for assisting the aforementioned nonionic surfactant to form a foam.

(Group B)

ethanol, isopropyl alcohol, propylene glycol, dipropylene glycol, glycerin, diglycerin, 1,3-butylene glycol, 1,2-pentanediol, 1,2-hexandiol, polyethylene glycol, polypropylene glycol.

The preferred aspect and content of alcohol are as described above.

The design method according to the present invention is characterized by selecting a nonionic surfactant selected from the group A within the range of 1 to 15 mass %, and selecting an alcohol selected from the group B within the range of 5 to 55 mass % so that a composition prepared by heating and cooling constitutional components with stirring is in a solubilized state.

The solubilized state refers to a state where a surfactant forms micells, and materials insoluble in a solvent is transparently and uniformly dissolved to form a single phase solution. Examples of the solubilized state include a microemulsion state. Microemulsion, which comprises emulsified particles with a fine particle diameter of 100 nm or less, is a thermodynamically stable micellar solution. A system may be considered to be in a solubilized state if its appearance is transparent. Alternatively, a solubilized state may be determined by measuring a particle size by the conventional method.

As demonstrated in Examples described below, the results showed that good foamability was able to be obtained when it was in a solubilized state. Therefore, it is important to design a composition for foaming so that the formulation is in a solubilized state.

In the design method according to the present invention, each of the aforementioned components is preferably selected so that the composition is still in a solubilized state both immediately after manufacture and 48 hours after manufacture or later (at room temperature). The external composition for screen foamers is preferred to maintain a solubilized state obtained immediately after manufacture even 48 hours after manufacture or later (at room temperature). Further, the external composition for screen foamers is particularly preferred to maintain a solubilized state obtained immediately after manufacture even 72 hours after manufacture or later (at room temperature).

The design method according to the present invention is suitable for designing an external medicament to be used without being removed after application. This is because constituent components for a base agent as described above and optional components other than an active ingredient for use in such a medicament are limited in view of safety.

That is, the design method according to the present invention is suitable for designing a composition in which the total content of the aforementioned nonionic surfactant, alcohol, water, and solvent is 90 mass % or more, preferably 95 mass % or more.

Below, an example of the design method according to the present invention will be described assuming that it is used as an external medicament.

(1) Selecting an active ingredient and the concentration thereof depending on the treatment target.

(2) Selecting a nonionic surfactant, an alcohol, and optionally a solvent, if desired (when the active ingredient selected in (1) is poorly soluble) within the aforementioned ranges, the remainder being water, to prepare a composition.

(3) Changing at least one of the types and amounts of those components selected in (2), and adjusting the remainder water accordingly to prepare another composition.

(4) Visually inspecting the resulting multiple compositions for the clarity and color of a solution immediately after manufacture and 48 hours (preferably 72 hours) after manufacture (at room temperature).

(5) Selecting a composition in which the solubilized state is maintained as a composition for foaming.

(6) Selecting appropriately a small amount of components which do not affect the solubilized state, such as a pH adjuster, an antiseptic agent, and the like, and which are commonly used in external medicaments.

The composition for screen foamers comprising a formulation obtained according to the design method of the present invention is a composition in a solubilized state which creates foam by virtue of a nonionic surfactant.

(6) Evaluation Method According to the Present Invention

The evaluation method according to the present invention is a method of evaluating the foamability of an aqueous external composition for screen foamers comprising 1 to 15 mass % of a nonionic surfactant selected from the group A as a foaming component, and 5 to 55 mass % of an alcohol selected from the group B, characterized by that the foamability of the composition is evaluated using the solubilized state of the composition as a guide.

That is, a composition prepared by selecting a specific nonionic surfactant and alcohol within the aforementioned ranges is evaluated for its solubilized state. The foamability with a screen foamer can be evaluated using the solubilized state as a guide.

The present evaluation method is preferably performed multiple times: immediately after manufacture of a composition and 48 hours after manufacture or later (at room temperature), preferably 72 hours after manufacture or later (at room temperature). The foamability is preferably considered as excellent if the solubilized state is maintained.

The aforementioned descriptions about the composition also apply to various preferred aspects of the design method and evaluation method according to the present invention.

EXAMPLE

Below, the present invention will be described in more detail with reference to Examples.

Surfactants (all are from NIKKOL) used for formulations and their HLBs are as follows.

Polyoxyethylene (9) lauryl ether (BL-9EX) 14.5

Polyoxyethylene (10) oleyl ether (BO-10V) 14.5

Polyoxyethylene (20) oleyl ether (BO-20V) 17.0
Polyoxyethylene (10) cetyl ether (BC-10) 13.5
Polyoxyethylene (23) cetyl ether (BC-23) 18.0
Polyoxyethylene (20) stearyl ether (BS-20) 18.0
Polyoxyethylene (20) behenyl ether (BB-20) 16.5
Polyethylene glycol monostearate (10 E.O.) (MYS-10V) 11.0
Polyethylene glycol monostearate (40 E.O.) (MYS-40V) 17.5
Polyethylene glycol monooleate (10 E.O.) (MYO-10V) 11.0
Polyoxyethylene (20) sorbitan monostearate (TS-10MV) 14.9
Polyoxyethylene (20) sorbitan monooleate (TO-10MV) 15.0
Polyoxyethylene (60) hydrogenated castor oil (HCO-60) 14.0
Polyoxyethylene (10) hydrogenated castor oil (HCO-10) 6.5
Polyoxyethylene (20) polyoxypropylene (8) cetyl ether (PBC-44) 12.5
Glyceryl monostearate (MGS-AMV) 4.0
Sorbitan monostearate (SS-10MV) 4.7

Example 1

The compositions for pump foamers according to the present invention and Comparative Examples were prepared according to the following formulations. That is, formulation components were each weighed, and heat-dissolved at 80° C., and then solubilized with stirring, and cooled with stirring to room temperature to obtain each composition. The conditions (the presence or absence of clouding and separation) of each composition were visually inspected immediately after preparation. Further, each composition was packed in a pump foamer container, and discharged onto a glass slide to observe foamability (foam volume) and foam quality (the texture fineness of foam), foam persistency (the conditions of foam after allowed to stand for 30 minutes at room temperature) and foam quality (the texture fineness of foam after allowed to stand for 30 minutes at room temperature). The formulation components shown in the table are expressed in mass % (the same for the following tables).

The evaluation was performed according to the following criteria.

(Clouding)
No clouding observed by visual inspection (Good)
Clouding observed by visual inspection (Poor)
(Separation)
No separation observed by visual inspection (Good)
Separation observed by visual inspection (Poor)
(Foamability)
Sufficient volume of foam obtained upon discharged (Good).
Less volume of foam obtained upon discharged (Fair)
No foam obtained upon discharged (Poor)
(Foam Quality)
Foam with fine texture obtained upon discharged (Good)
Foam with rough texture obtained upon discharged (Fair)
No foam obtained upon discharged (Poor)
(Persistency)
Large foam volume after standing at room temperature for 30 minutes (Good)
Less foam volume after standing at room temperature for 30 minutes (Fair)
No foam after standing at room temperature for 30 minutes (Poor)
(Foam Quality)
Foam with fine texture remained after standing at room temperature for 30 minutes (Good)
Foam with rough texture remained after standing at room temperature for 30 minutes (Fair)
No foam remained after standing at room temperature for 30 minutes (Poor)

Results are shown in Table 1 and FIG. 1.

TABLE 1

Table 1

| Formulation components | Composition 1 | Composition 2 | Composition 3 | Comparative Example 1 | Comparative Example 2 | Comparative Example 3 |
|---|---|---|---|---|---|---|
| Polyoxyethylene (10) oleylether | 7 | 1.5 | | | | 1.5 |
| Polyethylene glycol monostearate (10 E.O.) | | | 3.5 | 7 | | 5.5 |
| Polyoxyethylene (60) hydrogenated castor oil | | 5.5 | 3.5 | | 7 | |
| N-methyl-2-pyrrolidone | 5 | 5 | 5 | 5 | 5 | 5 |
| Diisopropyl adipate | 1 | 1 | 1 | 1 | 1 | 1 |
| Ethanol | 10 | 10 | 10 | 10 | 10 | 10 |
| Polyethylene glycol 400 | 25 | 25 | 25 | 25 | 25 | 25 |
| Glycerin | 5 | 5 | 5 | 5 | 5 | 5 |
| Water | 47 | 47 | 47 | 47 | 47 | 47 |
| State of composition (presence of clouding) | Good | Good | Good | Good | Poor | Poor |
| State of composition (presence of separation) | Good | Good | Good | Poor | Good | Good |
| Foamability immediately after discharged (foam volume) | Good | Good | Good | Fair | Poor | Poor |
| Foam quality immediately after discharged (fineness) | Good | Good | Good | Fair | Poor | Poor |
| Foam volume 30 minutes after discharged | Fair | Fair | Fair | Fair | Poor | Poor |
| Foam quality 30 minutes after discharged | Fair | Fair | Fair | Fair | Poor | Poor |

The results showed that the compositions 1 to 3 were in a solubilized state, and considered as compositions for pump foamers excellent in foamability, foam quality, and persistency. The results also showed that polyoxyethylene alkyl ether or polyoxyethylene alkenyl ether served as an excellent nonionic surfactant in the composition for pump foamers according to the present invention.

In contrast, Comparative Examples 1 to 3 were found not to be in a solubilized state (clouding or separation was observed), and did not show sufficient foamability, indicating that they can not be used as a composition for pump foamers.

These results suggest that foamability can be obtained when a composition is in a solubilized state, allowing it to be used as a composition for pump foamers.

Example 2

In order to study the effects of alcohol and solvent, Comparative Example with the following formulation was prepared according to the procedures used in Example 1. The results showed that it was a cloudy liquid (not in a solubilized state), and foam formation was not sufficient. These suggest that the composition is preferably in a clear single-phase liquid state, i.e., in a solubilized state. Further, the presence of alcohol and solvent was found to be preferred for foam formation.

TABLE 2

Table 2

| Formulation components | Comparative Example 4 |
|---|---|
| Polyethylene glycol monostearate (10 E.O.) | 7 |
| Water | 93 |

Example 3

Figure 2:
FIG. 2 shows images illustrating the results from Example 3.

The compositions according to the present invention were prepared according to the following formulation and the procedures used in Example 1. The state of each composition immediately after preparation was visually inspected (not cloudy: Good, cloudy: Poor). Each composition in an amount of 100 g was placed into a beaker, and stirred for 1 minute at 3000 rpm, and then allowed to stand for 2 minutes. The height (mm) of the resulting foam was measured when the foam-solution boundary became well defined. The foam quality was visually inspected (foam with fine texture obtained after stirring (Good); foam with rough texture obtained after stirring (Fair); no foam obtained after stirring (Poor)). Results are shown in Table 3 and FIG. 2. The external compositions according to the present invention showed outstanding foaming capability.

TABLE 3

Table 3

| Formulation components | Composition 4 | Composition 5 | Composition 6 | Composition 7 | Composition 8 |
|---|---|---|---|---|---|
| Polyoxyethylene (9) lauryl ether | 1.5 | | | | |
| Polyoxyethylene (23) cetyl ether | | 1.5 | | | |
| Polyoxyethylene (20) stearyl ether | | | 1.5 | | |
| Polyoxyethylene (20) oleylether | | | | 1.5 | |
| Polyoxyethylene (20) behenyl ether | | | | | 1.5 |
| Polyethylene glycol monostearate (40 E.O.) | 0.5 | 0.5 | 0.5 | 0.5 | 0.5 |
| Polyoxyethylene (60) hydrogenated castor oil | 0.5 | 0.5 | 0.5 | 0.5 | 0.5 |
| N-methyl-2-pyrrolidone | 6 | 6 | 6 | 6 | 6 |
| 1,3-butylene glycol | 15 | 15 | 15 | 15 | 15 |
| Hydrogenated soybean lecithin | 0.01 | 0.01 | 0.01 | 0.01 | 0.01 |
| Water | 76.49 | 76.49 | 76.49 | 76.49 | 76.49 |
| Clouding | Good | Good | Good | Good | Good |
| Foam height (mm) | 41.13 | 36.34 | 37.51 | 39.52 | 40.73 |
| Foam quality | Good | Good | Good | Good | Good |

Example 4

Figure 3:
FIG. 3 shows images illustrating the results from Example 4.

The compositions according to the present invention were prepared according to the following formulations and the procedures used in Example 3. Results are shown in Table 4 and FIG. 3. The external compositions according to the present invention showed outstanding foaming capability.

TABLE 4

Table 4

| Formulation components | Composition 9 | Composition 10 | Composition 11 |
|---|---|---|---|
| Polyoxyethylene (9) lauryl ether | 1.5 | 1.5 | 1.5 |
| Polyethylene glycol monostearate (40 E.O.) | 0.5 | 0.5 | 0.5 |
| Polyoxyethylene (60) hydrogenated castor oil | 0.5 | 0.5 | 0.5 |
| N-methyl-2-pyrrolidone | 6 | 6 | 6 |
| 1,3-butylene glycol | 15 | 15 | 15 |
| Hydrogenated soybean lecithin | 0.01 | | |
| Soybean lecithin | | 0.01 | |
| Hydrogenated soybean lecithin | | | 0.01 |
| Water | 76.49 | 76.49 | 76.49 |
| Clouding | Good | Good | Good |
| Foam height (mm) | 41.13 | 39.55 | 44.29 |
| Foam quality | Good | Good | Good |

Example 5

Figure 4:
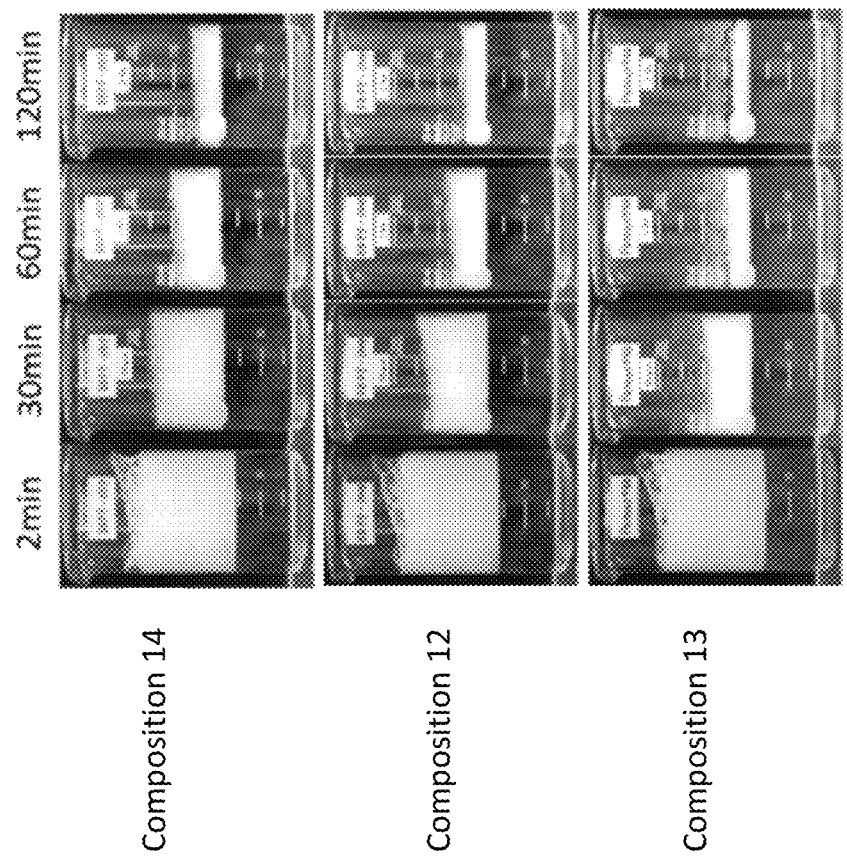
FIG. 4 shows images illustrating the results from Example 5.
Figure 5:
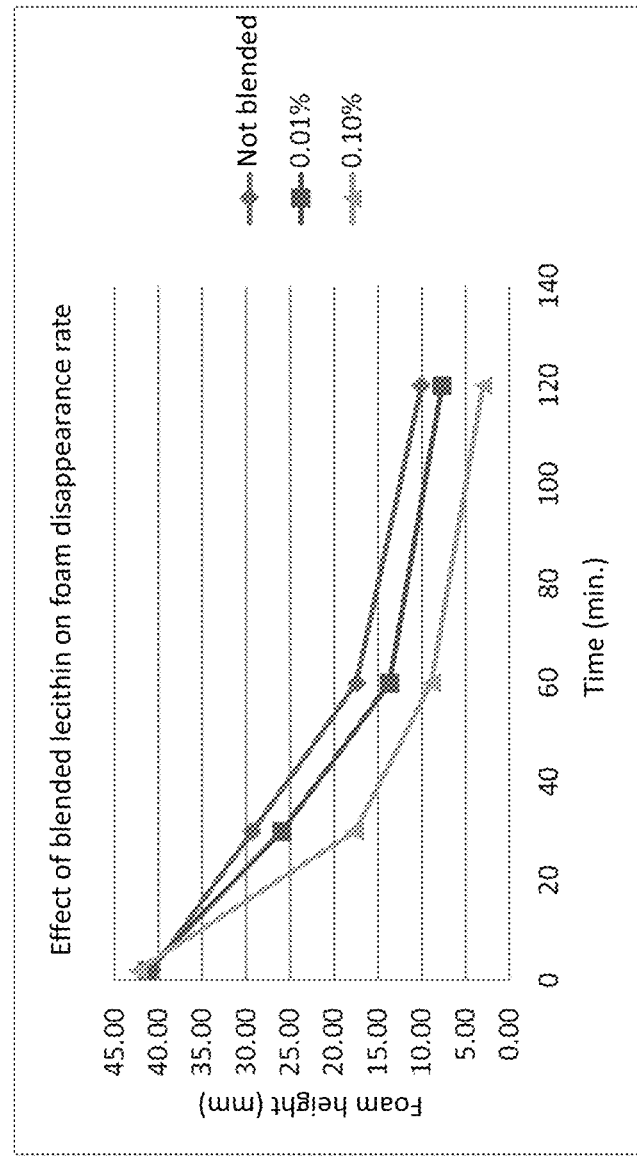
FIG. 5 shows a graph illustrating the results from Example 5.

The compositions according to the present invention were prepared according to the following formulation and the procedures used in Example 3. After foaming, they were allowed to stand at room temperature (for 2, 30, 60, and 120 minutes). The foam height was then measured, and how fast the foam disappeared was also studied. Results are shown in Table 5, FIG. 4 and FIG. 5.

TABLE 5

Table 5

| Formulation components | Composition 12 | Composition 13 | Composition 14 |
|---|---|---|---|
| Polyoxyethylene (9) lauryl ether | 1.5 | 1.5 | 1.5 |
| Polyethylene glycol monostearate (40 E.O.) | 0.5 | 0.5 | 0.5 |
| Polyoxyethylene (60) hydrogenated castor oil | 0.5 | 0.5 | 0.5 |
| N-methyl-2-pyrrolidone | 6 | 6 | 6 |
| 1,3-butylene glycol | 15 | 15 | 15 |
| Hydrogenated soybean lecithin | 0.01 | 0.1 | |
| Water | 76.49 | 76.4 | 76.5 |

TABLE 5-continued

Table 5

| Formulation components | Composition 12 | Composition 13 | Composition 14 |
|---|---|---|---|
| Clouding | Good | Good | Good |
| Foam height (mm) (immediately after stirring) | 41.24 | 42.34 | 40.71 |
| Foam quality (texture fineness) | Good | Good | Fair |

The results showed that foam quality was improved when phospholipid was added. The results also showed that addition of phospholipid accelerated the rate of foam disappearance in a case where they were allowed to stand at a room temperature. The compositions according to the present invention were found to be excellent in foaming capability, and characterized by creating a foam rapidly disappearing after foaming, and have excellent spreadability and low skin irritability.

Example 6

Figure 6:
FIG. 6 shows images illustrating the results from Example 6.
Figure 7:
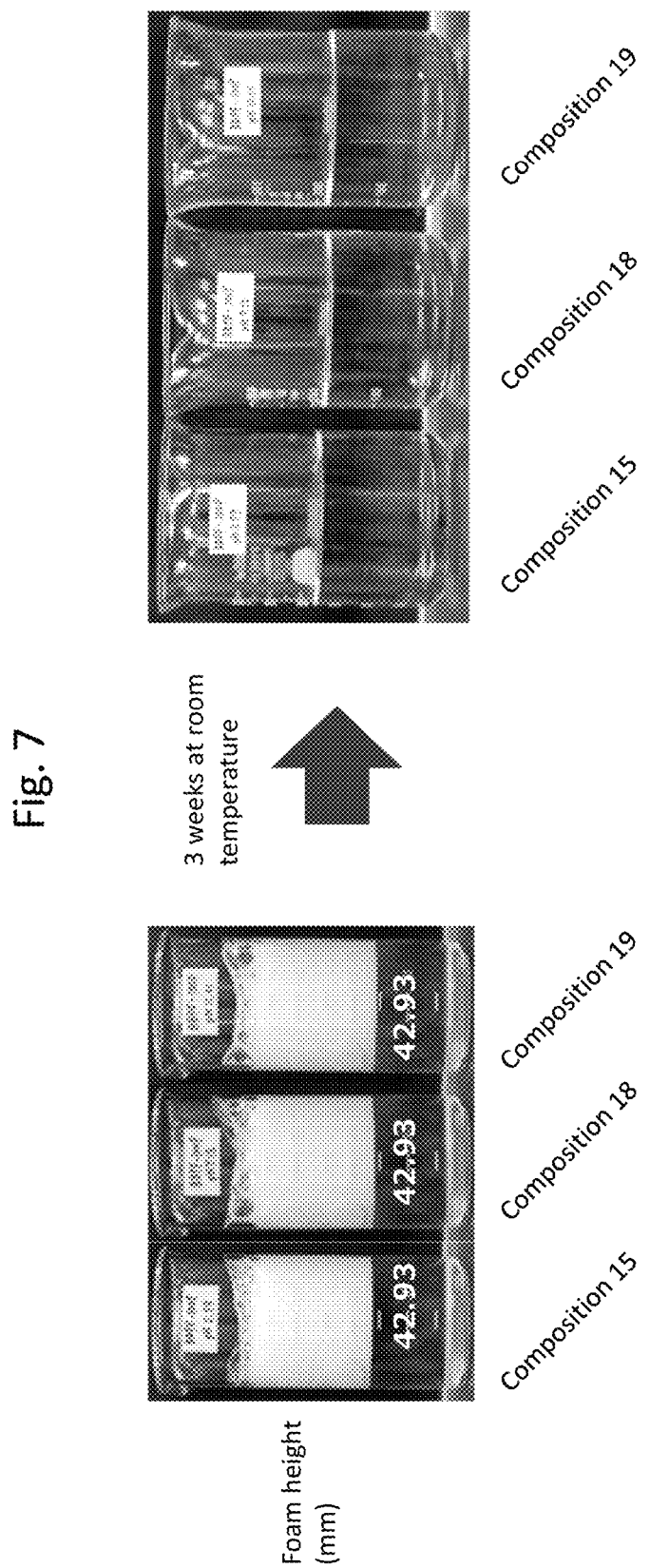
FIG. 7 shows images illustrating the results from Example 6 (after 3 weeks).

The compositions according to the present invention were prepared according to the following formulations and the procedures used in Example 3. Results are shown in Table 6 and FIG. 6. The compositions 15, 18, and 19 were each stirred in a beaker, and then allowed to stand for 3 weeks at room temperature. Then the conditions (precipitation) were observed. Results are shown in Table 6 and FIG. 7.

TABLE 6

Table 6

| Formulation components | Composition 15 | Composition 16 | Composition 17 | Composition 18 | Composition 19 |
|---|---|---|---|---|---|
| Polyoxyethylene (9) lauryl ether | 1.5 | 1.5 | 1.5 | 1.5 | 1.5 |
| Polyethylene glycol monostearate (40 E.O.) | 0.5 | 0.5 | 0.5 | 0.5 | 0.5 |
| Polyoxyethylene (60) hydrogenated castor oil | 0.5 | 0.5 | 0.5 | 0.5 | 0.5 |
| N-methyl-2-pyrrolidone | 6 | 6 | 6 | 6 | 6 |
| 1,3-butylene glycol | 15 | 15 | 15 | 15 | 15 |
| Hydrogenated soybean lecithin | 0.01 | 0.01 | 0.01 | 0.01 | 0.01 |
| 1% aqueous sodium hydroxide | | | | 0.25 | |
| 1% aqueous lactic acid | 2.5 | 1 | | | 1 |
| Water | 73.99 | 75.49 | 76.49 | 76.24 | 75.49 |
| pH | 2.59 | 3.66 | 4.3 | 7.12 | 11.11 |
| Clouding | Good | Good | Good | Good | Good |
| Foam height (mm) (immediately after stirring) | 42.93 | 42.89 | 41.13 | 42.93 | 42.93 |
| Foam quality (texture fineness) | Fair | Good | Good | Fair | Fair |
| Precipitate | Good | — | — | Good | Good |

The results showed that the compositions for pump foamers according to the present invention have excellent foaming capability regardless the acidity or alkalinity (pH). The results also indicated that the compositions for pump foamers according to the present invention did not show clouding even after allowed to stand for 3 weeks at room temperature after foaming. The compositions according to the present invention were found to be stable after application.

Example 7

The composition for pump foamers according to the present invention was prepared as in Example 3 according to the following formulation. This composition showed no clouding and good foamability.

TABLE 7

Table 7

| Formulation components | Composition 20 |
|---|---|
| Polyoxyethylene (9) lauryl ether | 1.5 |
| Polyethylene glycol monostearate (40 E.O.) | 0.5 |
| Polyoxyethylene (60) hydrogenated castor oil | 0.5 |
| N-methyl-2-pyrrolidone | 6 |
| 1,3-butylene glycol | 15 |
| Aqueous sodium hydroxide | q.s. |
| Disodium edetate | 0.2 |
| Water | q.s. |

Sodium hydroxide was used to adjust the pH to weakly acidic, the remainder being water.

Example 8

The composition for pump foamers according to the present invention was prepared as in Example 3 according to the following formulation. This composition showed no clouding and good foamability.

TABLE 8

Table 8

| Formulation components | Composition 21 |
|---|---|
| Polyoxyethylene (9) lauryl ether | 1.5 |
| Polyethylene glycol monostearate (40 E.O.) | 0.5 |
| Polyoxyethylene (60) hydrogenated castor oil | 0.5 |
| N-methyl-2-pyrrolidone | 6 |
| 1,3-butylene glycol | 15 |
| Aqueous sodium hydroxide | q.s. |
| Hydrogenated soybean lecithin | 0.01 |
| Disodium edetate | 0.2 |
| Water | q.s. |

Sodium hydroxide was used to adjust the pH to weakly acidic, the remainder being water.

Example 9

The compositions for pump foamers according to the present invention were prepared according to the following formulations and the procedures used in Example 1. The solubilized states of these compositions were visually inspected immediately after preparation. Further, these compositions each packed in a pump foamer container were discharged onto glass slides, and the state of foam (foamability (foam volume) and foam quality (texture fineness of foam)) was observed.

The evaluation was performed according to the following criteria.
(Solubilization)
Clouding or separation not observed by visual inspection (Good)
Clouding or separation observed by visual inspection (Poor)
(Foam)
Sufficient foam volume and fine foam quality (Good)
Sufficient foam volume but rough foam quality or insufficient foam volume (Fair)

No Foaming (Poor)

The results showed that excellent foamability was able to be obtained when they were in a solubilized state.

The presence of clouding, foamability, and foam quality were evaluated according to the method and criteria similar to those used in Example 1. The results showed that polyoxyethylene alkyl ether and/or polyoxyethylene alkenyl ether were particularly preferred as a nonionic surfactant when a high content of a solvent was included (for example, 10 mass % or more).

TABLE 9

| Formulation components | Composition 22 | Composition 23 | Composition 24 | Composition 25 | Composition 26 | Composition 27 | Comparative Example 5 | Comparative Example 6 |
|---|---|---|---|---|---|---|---|---|
| Polyoxyethylene (9) lauryl ether | 7 | | | | | | | |
| Polyoxyethylene (10) oleylether | | | 7 | | | | | |
| Polyoxyethylene (10) cetyl ether | | | | 7 | | | | |
| Polyethylene glycol monostearate (10 E.O.) | | | | | | | | 7 |
| Polyethylene glycol monooleate (10 E.O.) | | | | | | | 7 | |
| Polyoxyethylene (20) sorbitan monooleate | | | | | 7 | | | |
| Polyoxyethylene (20) sorbitan monostearate | | | | | | 7 | | |
| Polyoxyethylene (60) hydrogenated castor oil | | 7 | | | | | | |
| N-methyl-2-pyrrolidone | | | | 5 | 5 | 5 | 5 | 5 |
| Diisopropyl adipate | | | | 1 | 1 | 1 | 1 | 1 |
| Ethanol | | | | 5 | 5 | 5 | 5 | 5 |
| Water | 93 | 93 | 82 | 82 | 82 | 82 | 82 | 93 |
| Solubilization | Good | Good | Good | Good | Good | Good | Poor | Poor |
| Foam | Good | Good | Good | Good | Good | Good | Good | Poor |

Example 10

The compositions having the following formulations were prepared according to the procedures used in Example 9. The solubilized state and foam state were evaluated according to the method and criteria similar to those used in Example 9. The results indicated that the compositions according to the present invention showed a potential for use as pharmaceutical compositions for pump foamers comprising various active ingredients.

TABLE 10

| Formulation components | Composition 28 | Composition 29 | Comparative Example 7 | Composition 30 | Composition 31 |
|---|---|---|---|---|---|
| Polyoxyethylene (9) lauryl ether | 1.5 | 1.5 | 1.5 | 1.5 | 1.5 |
| Polyethylene glycol monostearate (10 E.O.) | 0.5 | 0.5 | 0.5 | 0.5 | 0.5 |
| Polyoxyethylene (60) hydrogenated castor oil | 0.5 | 0.5 | 0.5 | 0.5 | 0.5 |
| N-methyl-2-pyrrolidone | 6 | 6 | 6 | 6 | 6 |
| 1,3-butylene glycol | 15 | 15 | 15 | 15 | 15 |
| Betamethasone butyrate propionate | 0.05 | | | | |
| Tretinoin tocoferil | | 0.05 | | | |
| Adapalene | | | 0.05 | | |
| Heparinoid | | | | 0.1 | |
| Urea | | | | | 1 |
| Hydrogenated soybean lecithin | 0.01 | 0.01 | 0.01 | 0.01 | 0.01 |
| Water | 76.44 | 76.44 | 76.44 | 76.39 | 75.49 |
| Solubilization | Good | Good | Poor | Good | Good |
| Foam | Good | Good | Good | Good | Good |

Example 11

The compositions having the following formulations were prepared according to the procedures used in Example 1.

TABLE 11

| Formulation components | Composition 32 | Composition 33 | Composition 34 | Composition 35 |
|---|---|---|---|---|
| N-methyl-2-pyrrolidone | 35 | 35 | 35 | 35 |
| 1,3-butylene glycol | 15 | 15 | 15 | 15 |
| Polyoxyethylene (9) lauryl ether | 1 | | 10 | |
| Polyoxyethylene (20) polyoxypropylene (8) cetyl ether | | 1 | | 10 |
| Water | 49 | 49 | 40 | 40 |
| Clouding | Good | Good | Good | Good |
| Foamability | Good | Good | Good | Good |
| Foam quality | Good | Fair | Good | Fair |

Example 12

The compositions having the following formulations were prepared according to the procedures used in Example 9. The solubilized state and foam state were evaluated according to the method and criteria similar to those used in Example 9. The results showed that an antifungal agent as an active ingredient was able to be brought into a solubilized state, and such a medicament had excellent foamability.

TABLE 12

| Formulation components | Composition 36 | Composition 37 |
|---|---|---|
| Terbinafine hydrochloride | 1 | |
| Ketoconazole | | 0.1 |
| N-methyl-2-pyrrolidone | 6 | 12 |
| 1,3-butylene glycol | 15 | 40 |
| Polyoxyethylene (9) lauryl ether | 1.5 | 1.5 |
| Polyethylene glycol monostearate (40 E.O.) | 0.5 | 0.5 |
| Polyoxyethylene (60) hydrogenated castor oil | 0.5 | 0.5 |

TABLE 12-continued

Table 12

| Formulation components | Composition 36 | Composition 37 |
|---|---|---|
| Hydrogenated soybean lecithin | 0.01 | 0.01 |
| Water | 75.49 | 45.39 |
| Solubilization | Good | Good |
| Foam | Good | Good |

Example 13

Figure 8:
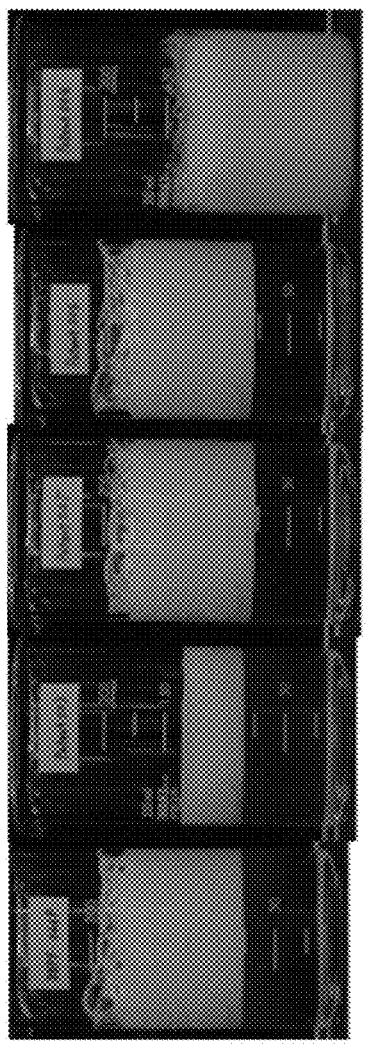
FIG. 8 shows images illustrating the results from Example 13.

The compositions for the pump foamers according to the present invention were prepared as in Example 6 according to the following formulations. Results are shown in Table 13 and FIG. 8. The results showed that solubilized states were able to be obtained by using various solvents, and the compositions in solubilized states had excellent foamability.

TABLE 13

Table 13

| Formulation components | Composition 38 | Composition 39 | Composition 40 | Composition 41 | Comparative Example 8 |
|---|---|---|---|---|---|
| N-methyl-2-pyrrolidone | 6 | | | | |
| Benzyl alcohol | | 6 | | | |
| Propylene carbonate | | | 6 | | |
| Ethanol | | | | 6 | |
| Crotamiton | | | | | 6 |
| Polyoxyethylene (9) lauryl ether | 1.5 | 1.5 | 1.5 | 1.5 | 1.5 |
| Polyethylene glycol monostearate (40 E.O.) | 1.5 | 1.5 | 1.5 | 1.5 | 1.5 |
| Polyoxyethylene (60) hydrogenated castor oil | 1.5 | 1.5 | 1.5 | 1.5 | 1.5 |
| 1,3-butylene glycol | 15 | 15 | 15 | 15 | 15 |
| Polyethylene glycol 400 | 2.5 | 2.5 | 2.5 | 2.5 | 2.5 |
| D-sorbitol | 0.25 | 0.25 | 0.25 | 0.25 | 0.25 |
| Water | 71.75 | 71.75 | 71.75 | 71.75 | 71.75 |
| Clouding | Good | Good | Good | Good | Poor |

TABLE 13-continued

Table 13

| Formulation components | Composition 38 | Composition 39 | Composition 40 | Composition 41 | Comparative Example 8 |
|---|---|---|---|---|---|
| Foam height (mm) (immediately after stirring) | 39.03 | 12.51 | 38.76 | 37.79 | 6.95 |
| Foam quality (texture fineness) | Good | Good | Good | Good | Poor |

Example 14

Figure 9:
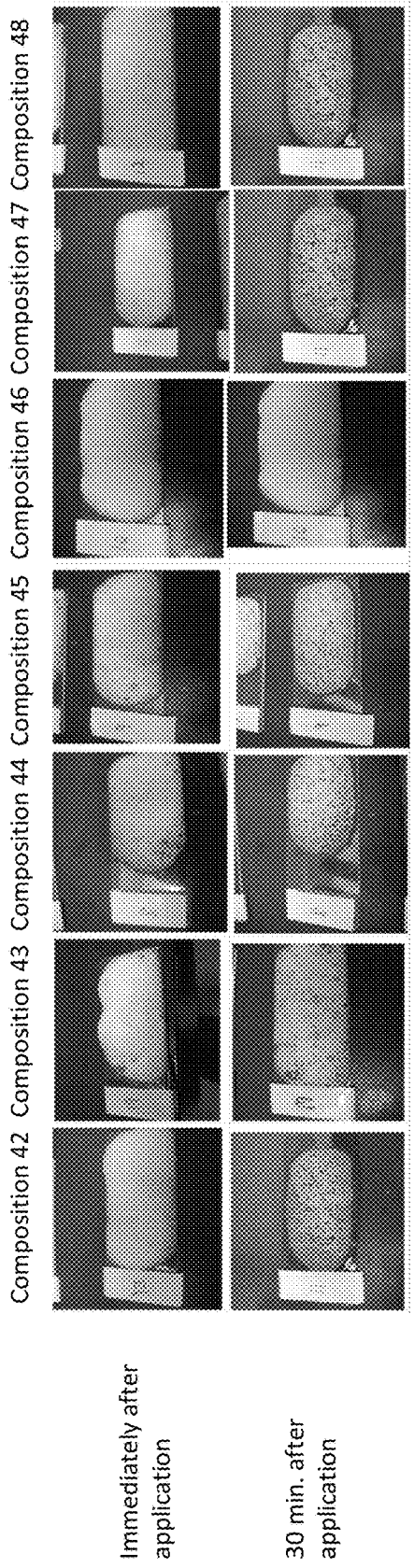
FIG. 9 shows images illustrating the results from Example 14.

The compositions for pump foamers were prepared as in Example 1 according to the following formulations. Results are shown in Table 14 and FIG. 9.

TABLE 14

Table 14

| Formulation components | Composition 42 | Composition 43 | Composition 44 | Composition 45 | Composition 46 | Composition 47 | Composition 48 |
|---|---|---|---|---|---|---|---|
| Polyoxyethylene (10) oleylether | 7 | 1.5 | 1.5 | 1.5 | 1.5 | 1.5 | 1.5 |
| Polyethylene glycol monostearate (10 E.O.) | | 3.5 | 3.5 | 3.5 | 3.5 | 3.5 | 3.5 |
| Polyoxyethylene (60) hydrogenated castor oil | | 5.5 | 2 | 2 | 2 | 2 | 2 |
| N-methyl-2-pyrrolidone | 5 | 5 | 5 | 5 | 5 | 5 | 5 |
| Diisopropyl adipate | 1 | 1 | 1 | 1 | 1 | 1 | 1 |
| Ethanol | 10 | 10 | 10 | | | | |
| 1,3-butylene glycol | | | | 10 | | | |
| Polyethylene glycol 400 | 25 | 25 | | | 10 | | |
| Glycerin | 5 | 5 | | | | 10 | |
| Propylene glycol | | | | | | | 10 |
| Water | 47 | 47 | 77 | 77 | 77 | 77 | 77 |
| State of composition (presence of clouding) | Good | Good | Good | Good | Good | Good | Good |
| State of composition (existence of separation) | Good | Good | Good | Good | Good | Good | Good |
| Foamability immediately after discharged (foam volume) | Good | Good | Good | Good | Good | Good | Good |
| Foam quality immediately after discharged | Good | Good | Fair | Good | Good | Good | Good |
| Foam volume 30 minutes after discharged | Fair | Fair | Fair | Good | Good | Fair | Fair |
| Foam quality 30 minutes after discharged | Fair | Fair | Fair | Fair | Fair | Fair | Fair |

The results showed that the compositions according to the present invention had excellent foam properties.

Example 15

Figure 10:
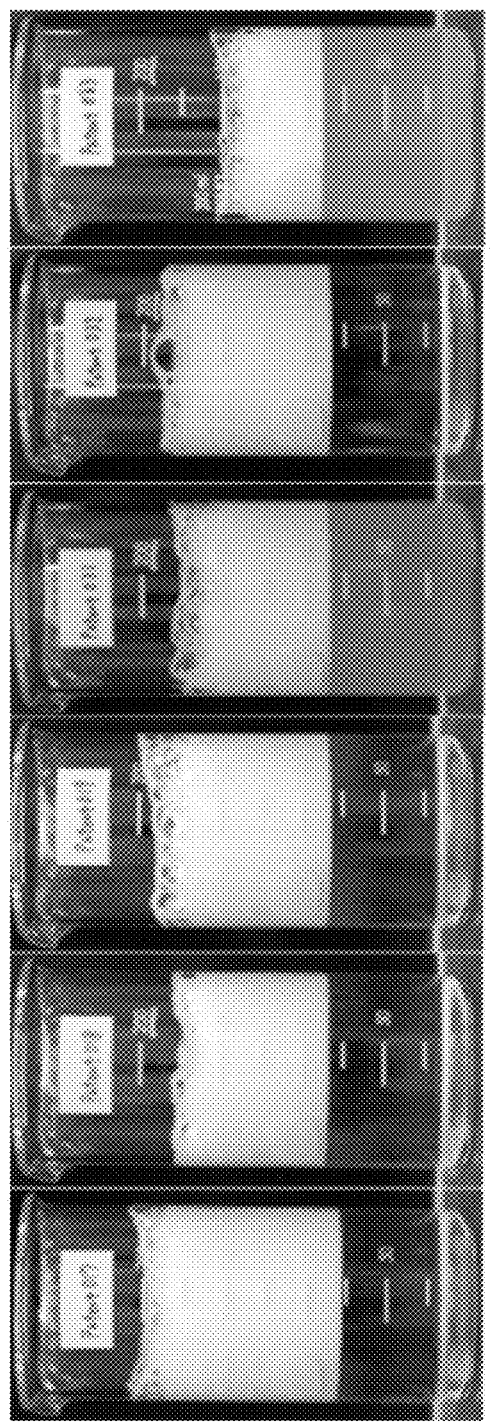
FIG. 10 shows images illustrating the results from Example 15.

The compositions according to the present invention were prepared according to the following formulations and the procedures used in Example 1. The state of each composition immediately after preparation was visually inspected (not cloudy: Good, cloudy: Poor). A composition in an amount of 100 g was placed into a beaker, and stirred for 1 minute at 3000 rpm, and then allowed to stand for 2 minutes. The height (mm) of the resulting foam was measured when the foam-solution boundary became well defined. The foam quality was visually inspected (foam with fine texture obtained after stirring (Good); foam with rough texture obtained after stirring (Fair); no foam obtained after stirring (Poor)). Precipitation after allowed to stand for one week at room temperature was also visually inspected (no precipitation: Good, cloudy: Fair, precipitated: Poor). Results are shown in Table 15 and FIG. 10. The external compositions according to the present invention showed outstanding foaming capability. Further, the compositions according to the present invention did not show the presence of a precipitate after allowed to stand for one week at room temperature. In contrast, a precipitate was observed when the composition for pump foamers comprising lauric acid diethanolamide was used.

TABLE 15

| Formulation components | Composition 49 | Composition 50 | Composition 51 | Composition 52 | Composition 53 | Composition 54 |
|---|---|---|---|---|---|---|
| Polyoxyethylene (9) lauryl ether | 1.5 | 1.5 | 1.5 | 1.5 | 1.5 | 1.5 |
| Polyethylene glycol monostearate (40 E.O.) | 0.5 | 0.5 | 0.5 | 0.5 | 0.5 | 0.5 |
| Polyoxyethylene (60) hydrogenated castor oil | 0.5 | 0.5 | 0.5 | 0.5 | 0.5 | 0.5 |
| N-methyl-2-pyrrolidone | 6 | 6 | 6 | 6 | 6 | 6 |
| Ethanol | 15 | | | | | |
| 1,3-butylene glycol | | 15 | | | | 15 |
| Polyethylene glycol 400 | | | 15 | | | 15 |
| Glycerin | | | | 15 | | 15 |
| Propylene glycol | | | | | 15 | |
| Water | 76.5 | 76.5 | 76.5 | 76.5 | 76.5 | 46.5 |
| Clouding | Good | Good | Good | Good | Good | Good |
| Foam height (mm) | 43.95 | 44.71 | 47.24 | 43.39 | 41.77 | 33.75 |
| Foam quality | Good | Good | Good | Good | Good | Good |
| Precipitate (one week at room temperature) | Good | Good | Good | Good | Good | Good |

Example 16

Figure 11:
FIG. 11 shows images illustrating the results from Example 16.

The compositions according to the present invention were prepared according to the following formulations and the procedures used in Example 15, and then evaluated. Results are shown in Table 16 and FIG. 11. The external compositions according to the present invention showed outstanding foaming capability.

TABLE 16

| Formulation components | Composition 55 | Composition 56 | Composition 57 | Composition 58 | Composition 59 |
|---|---|---|---|---|---|
| Polyoxyethylene (9) lauryl ether | 1.5 | 1.5 | 1.5 | 1.5 | 1.5 |
| Polyethylene glycol monostearate (40 E.O.) | 0.5 | 0.5 | 0.5 | 0.5 | 0.5 |
| Polyoxyethylene (60) hydrogenated castor oil | 0.5 | 0.5 | 0.5 | 0.5 | 0.5 |
| N-methyl-2-pyrrolidone | 6 | 6 | 6 | 6 | 6 |
| 1,3-butylene glycol | 15 | | | | |
| Propylene glycol | | 15 | | | |
| Glycerin | | | 15 | | |
| Polyethylene glycol 400 | | | | 15 | |
| Polyethylene glycol 4000 | | | | | 15 |
| Hydrogenated soybean lecithin | 0.01 | 0.01 | 0.01 | 0.01 | 0.01 |
| Water | 76.49 | 76.49 | 76.49 | 76.49 | 76.49 |
| Clouding | Good | Good | Good | Poor | Poor |
| Foam height (mm) | 41.13 | 42.26 | 42.66 | 42.32 | 36.62 |
| Foam quality | Good | Good | Good | Good | Good |
| Precipitate (one week at room temperature) | Good | Good | Good | Poor | Good |

Example 17

Figure 12:
FIG. 12 shows images illustrating the results from Example 17.

The compositions according to the present invention were prepared according to the following formulations and the procedures used in Example 3, and then evaluated. Results are shown in Table 17 and FIG. 12. The external compositions according to the present invention showed outstanding foaming capability.

TABLE 17

| Formulation components | Composition 60 | Composition 61 | Composition 62 | Composition 63 |
|---|---|---|---|---|
| Polyoxyethylene (9) lauryl ether | 1.5 | 1.5 | 1.5 | 1.5 |
| Polyethylene glycol monostearate (40 E.O.) | 0.5 | 0.5 | 0.5 | 0.5 |
| Polyoxyethylene (60) hydrogenated castor oil | 0.5 | 0.5 | 0.5 | 0.5 |
| N-methyl-2-pyrrolidone | 6 | 6 | 6 | 6 |
| 1,3-butylene glycol | 15 | 15 | 15 | 15 |
| Hydrogenated soybean lecithin | 0.01 | | | |
| Soybean lecithin | | 0.01 | | |
| Hydroxylation soybean lecithin | | | 0.01 | |
| Ceramide | | | | 0.01 |
| Water | 76.49 | 76.49 | 76.49 | 76.49 |
| Clouding | Good | Good | Good | Poor |
| Foam height (mm) | 41.13 | 39.55 | 44.29 | 42.38 |
| Foam quality | Good | Good | Good | Good |

Example 18

The composition according to the present invention was prepared according to the following formulation and the procedures used in Example 15. Results are shown in Table 18. The external composition according to the present invention showed outstanding foaming capability. The formulation components shown in the table are expressed in mass %. The composition according to the present invention was found to have excellent foam properties. In contrast, Comparative Examples showed precipitation.

TABLE 18

| Formulation components | Composition 64 | Comparative Example 9 | Comparative Example 10 |
|---|---|---|---|
| Polyoxyethylene (9) lauryl ether | 1.5 | | |
| Polyethylene glycol monostearate (40 E.O.) | 0.5 | | |

TABLE 18-continued

Table 18

| Formulation components | Composition 64 | Comparative Example 9 | Comparative Example 10 |
|---|---|---|---|
| Polyoxyethylene (60) hydrogenated castor oil | 0.5 | | |
| Cetyl sodium sulfate | | 0.5 | |
| Laurie acid diethanolamide | | | 1.5 |
| N-methyl-2-pyrrolidone | 6 | 6 | 6 |
| 1,3-butylene glycol | 15 | 15 | 15 |
| Glycerin | 15 | 15 | 15 |
| Polyethylene glycol 400 | 15 | 15 | 15 |
| Water | 46.50 | 48.50 | 47.50 |
| Clouding | Good | Good | Good |
| Foam height (mm) (immediately after stirring) | 33.75 | 57.11 | 38.19 |
| Foam quality (texture fineness) | Good | Good | Good |
| Standing at room temperature for one week after stirring | Good | Poor | Poor |

Example 19

The composition according to the present invention was prepared according to the following formulation and the procedures used in Example 1. The external composition according to the present invention showed outstanding foaming capability.

TABLE 19

Table 19

| Formulation components | Composition 65 |
|---|---|
| Polyoxyethylene (9) lauryl ether | 1.5 |
| Polyethylene glycol monostearate (40 E.O.) | 0.5 |
| Polyoxyethylene (60) hydrogenated castor oil | 0.5 |
| N-methyl-2-pyrrolidone | 6 |
| 1,3-butylene glycol | 15 |
| Glycerin | 15 |
| Polyethylene glycol 400 | 15 |
| Hydrogenated soybean lecithin | 0.01 |
| Water | 46.49 |

Example 20

The compositions according to the present invention were prepared according to the following formulations and the procedures used in Example 3, and then the foam height and foam quality were evaluated. Results are shown in Table 20. The external compositions according to the present invention showed outstanding foaming capability.

TABLE 20

Table 20

| Formulation components | Composition 66 | Composition 67 | Composition 68 | Composition 69 | Composition 70 |
|---|---|---|---|---|---|
| Polyoxyethylene (9) lauryl ether | 1.5 | 1.5 | 1.5 | 1.5 | 1.5 |
| Polyethylene glycol monostearate (40 E.O.) | | 1.5 | | | |
| Polyoxyethylene (60) hydrogenated castor oil | | | | 1.5 | 1.5 |
| Glyceryl monostearate (MGS-AMV) | 1.5 | | 1.5 | 1.5 | |
| Sorbitan monostearate (SS-10MV) | | 1.5 | | | 1.5 |
| N-methyl-2-pyrrolidone | 6 | 6 | 6 | 6 | 6 |
| 1,3-butylene glycol | 15 | 15 | 15 | 15 | 15 |
| Polyethylene glycol 400 | 2.5 | 2.5 | 2.5 | 2.5 | 2.5 |
| D-sorbitol | 0.25 | 0.25 | 0.25 | 0.25 | 0.25 |
| Water | 73.25 | 73.25 | 71.75 | 71.75 | 71.75 |
| Foam height (mm) | 34.12 | 40.20 | 43.52 | 44.99 | 40.13 |
| Foam quality | Fair | Fair | Good | Good | Good |

Example 21

The compositions for pump foamers according to the present invention were produced as in Example 9 according to the following formulations, and then evaluated. Changes in the solubilized state and foam state over time when stored at room temperature were also observed. The results showed that foamability was excellent when the content of alcohol was 10 mass %. The results also showed that the solubilized state was maintained, and good foamability was obtained in such a case.

TABLE 21

Table 21

| Formulation components | Composition 71 | Composition 72 | Composition 73 | Composition 74 | Composition 75 | Composition 76 | Composition 77 |
|---|---|---|---|---|---|---|---|
| Betamethasone butyrate propionate | 0.05 | 0.05 | 0.05 | 0.05 | 0.05 | 0.05 | 0.05 |
| Polyethylene glycol monooleate (10 EO.) | 1.5 | 1.5 | 1.5 | 1.5 | 1.5 | 7 | |
| Polyethylene glycol monostearate (10 E.O.) | 3.5 | 3.5 | 3.5 | 3.5 | 3.5 | | |
| Polyoxyethylene (60) hydrogenated castor oil | 2 | 2 | 2 | 2 | 2 | | 7 |
| N-methyl-2-pyrrolidone | 5 | 5 | 5 | 5 | 5 | 5 | 5 |
| Diethyl adipate | 1 | 1 | 1 | 1 | 1 | 1 | 1 |
| Ethanol | 10 | | | | | 10 | 10 |
| 1,3-butylene glycol | | 10 | | | | | |
| Polyethylene glycol 400 | | | 10 | | | 25 | 25 |
| Glycerin | | | | 10 | | 5 | 5 |
| Propylene glycol | | | | | 10 | | |
| Water | 76.95 | 76.95 | 76.95 | 76.95 | 76.95 | 46.95 | 46.95 |

TABLE 21-continued

Table 21

| | | | | | | | |
|---|---|---|---|---|---|---|---|
| Solubilization | Good | Good | Good | Good | Good | Good | Good |
| Foam | Good | Good | Good | Good | Good | Good | Good |
| Change over time | | | Clouded after 5 days. Foaming. | | | | |

| Formulation components | Composition 78 | Composition 79 | Comparative Example 11 | Comparative Example 12 | Comparative Example 13 |
|---|---|---|---|---|---|
| Betamethasone butyrate propionate | 0.05 | 0.05 | 0.05 | 0.05 | 0.05 |
| Polyethylene glycol monooleate (10 EO.) | 1.5 | | | 1.5 | 1.5 |
| Polyethylene glycol monostearate (10 E.O.) | | 3.5 | 3.5 | 3.5 | 3.5 |
| Polyoxyethylene (60) hydrogenated castor oil | 5.5 | 3.5 | 3.5 | 2 | 2 |
| N-methyl-2-pyrrolidone | 5 | 5 | 5 | 5 | 5 |
| Diethyl adipate | 1 | 1 | 1 | 1 | 1 |
| Ethanol | 10 | 10 | 5 | | |
| 1,3-butylene glycol | | | | | 5 |
| Polyethylene glycol 400 | 25 | 25 | | | |
| Glycerin | 5 | 5 | | | |
| Propylene glycol | | | | | |
| Water | 46.95 | 46.95 | 81.95 | 86.95 | 81.95 |
| Solubilization | Good | Good | Good | Poor | Good |
| Foam | Good | Good | Good | Good | Good |
| Change over time | Clouded after 5 days. Foaming. | | Clouded on Day 5. No foaming. | | Clouded on Day 2. No foaming. |

Example 22

The compositions having the following formulations were prepared as in Example 9, and then evaluated. The results showed that foamability is excellent when 1,3-butylene glycol was used. The formulation components shown in the table are expressed in mass %.

TABLE 22

Table 22

| Formulation components | Composition 80 | Composition 81 | Composition 82 | Composition 83 | Composition 84 |
|---|---|---|---|---|---|
| Polyoxyethylene (9) lauryl ether | 1.5 | 1.5 | 1.5 | 1.5 | 1.5 |
| Polyethylene glycol monostearate (10 E.O.) | 0.5 | 0.5 | 0.5 | 0.5 | 0.5 |
| Polyoxyethylene (60) hydrogenated castor oil | 0.5 | 0.5 | 0.5 | 0.5 | 0.5 |
| N-methyl-2-pyrrolidone | 6 | 6 | 6 | | |
| 1,3-butylene glycol | 15 | 15 | 15 | 15 | 12 |
| Hydrogenated soybean lecithin | 0.01 | 0.1 | | | |
| Water | 76.49 | 76.4 | 76.5 | 82.5 | 85.5 |
| Solubilization | Good | Good | Good | Good | Good |
| Foam | Good | Good | Good | Good | Good |

Example 23

The compositions having the following formulations were prepared as in Example 9, and then evaluated. They were also evaluated similarly three days after manufacture (stored at room temperature). The results showed that various nonionic surfactants were able to be used for the compositions according to the present invention. Further, polyoxyethylene alkyl ether and/or polyoxyethylene alkenyl ether were found to be particularly preferred.

TABLE 23

Table 23

| Formulation components | Composition 85 | Composition 86 | Composition 87 | Composition 88 |
|---|---|---|---|---|
| Betamethasone butyrate propionate | 0.05 | 0.05 | 0.05 | 0.05 |
| N-methyl-2-pyrrolidone | 5 | 5 | 5 | 5 |
| Diisopropyl adipate | 1 | 1 | 1 | 1 |
| Ethanol | 10 | 10 | 10 | 10 |
| Polyethylene glycol 400 | 25 | 25 | 25 | 25 |
| Glycerin | 5 | 5 | 5 | 5 |
| Polyoxyethylene (9) lauryl ether | 7 | | | |
| Polyoxyethylene (10) cetyl ether | | 7 | | |
| Polyoxyethylene (20) sorbitan monostearate | | | 7 | |
| Polyoxyethylene (20) sorbitan monooleate | | | | 7 |
| Water | 46.95 | 46.95 | 46.95 | 46.95 |
| Solubilization (immediately after manufacture) | Good | Good | Good | Good |
| Foam (immediately after manufacture) | Good | Good | Fair | Good |
| Solubilization (three days after manufacture) | Good | Fair | Fair | Fair |
| Foam (three days after manufacture) | Good | Fair | Fair | Fair |

Example 24

The compositions having the following formulations were prepared as in Example 9, and then evaluated. The results showed that foaming agents were able to be manufactured using monohydric or polyhydric alcohol. Foamability was found to be particularly excellent when polyhydric alcohol was used.

TABLE 24

| Formulation components | Composition 89 | Composition 90 | Composition 91 | Composition 92 | Composition 93 | Composition 94 | Composition 95 |
|---|---|---|---|---|---|---|---|
| Betamethasone butyrate propionate | 0.05 | 0.05 | 0.05 | 0.05 | 0.05 | 0.05 | 0.05 |
| N-methyl-2-pyrrolidone | 5 | 5 | 5 | 5 | 5 | 5 | 5 |
| Diisopropyl adipate | 1 | 1 | 1 | 1 | 1 | 1 | 1 |
| Ethanol | 25 | | | | | | |
| 1,3-butylene glycol | | 25 | 50 | | | | |
| Polyethylene glycol 400 | | | | 25 | | | |
| Propylene glycol | | | | | 25 | 50 | |
| Glycerin | | | | | | | 25 |
| Polyoxyethylene (10) oleylether | 1.5 | 1.5 | 1.5 | 1.5 | 1.5 | 1.5 | 1.5 |
| Polyethylene glycol monostearate (10 E.O.) | 3.5 | 3.5 | 3.5 | 3.5 | 3.5 | 3.5 | 3.5 |
| Polyoxyethylene (60) hydrogenated castor oil | 2 | 2 | 2 | 2 | 2 | 2 | 2 |
| Water | 61.95 | 61.95 | 36.95 | 61.95 | 61.95 | 36.95 | 61.95 |
| Solubilization | Good | Good | Good | Poor | Good | Good | Poor |
| Foam | Fair | Good | Good | Good | Good | Good | Good |

Example 25

The compositions having the following formulations were prepared as in Example 9, and then evaluated. The results showed that forming agents including the high contents of various polyhydric alcohols were able to be manufactured.

TABLE 25

| Formulation components | Composition 96 | Composition 97 | Composition 98 | Composition 99 | Composition 100 |
|---|---|---|---|---|---|
| Betamethasone butylate propionate | 0.05 | 0.05 | 0.05 | 0.05 | 0.05 |
| N-methyl-2-pyrrolidone | 6 | 6 | 6 | 6 | 6 |
| Crotamiton | 0.5 | 0.5 | 0.5 | 0.5 | 0.5 |
| 1,3-butylene glycol | 15 | 40 | 15 | 15 | 15 |
| Propylene glycol | | | | | 5 |
| Glycerin | | | 20 | 40 | |
| Polyoxyethylene (9) lauryl ether | 1.5 | 1.5 | 1.5 | 1.5 | 1.5 |
| Polyoxyethylene (20) polyoxypropylene (8) cetyl ether | 0.5 | 0.5 | 0.5 | 0.5 | 0.5 |
| Polyoxyethylene (60) hydrogenated castor oil | 0.5 | 0.5 | 0.5 | 0.5 | 0.5 |
| Hydrogenated soybean lecithin | 0.01 | 0.01 | 0.01 | 0.01 | 0.01 |
| Methyl parahydroxybenzoate | 0.2 | 0.2 | 0.2 | 0.2 | 0.2 |
| Sodium hydroxide | q.s. | q.s. | q.s. | q.s. | q.s. |
| Disodium edetate | 0.2 | 0.2 | 0.2 | 0.2 | 0.2 |
| Water | q.s. | q.s. | q.s. | q.s. | q.s. |
| Solubilization | Good | Good | Good | Good | Good |
| Foam | Good | Good | Good | Good | Good |

Sodium hydroxide was used to adjust the pH to weakly acidic, the remainder being water.

Example 26

The compositions having the following formulations were prepared as in Example 9, and then evaluated. The results showed that forming agents including the various concentrations of 1,3-butylene glycol were able to be manufactured.

TABLE 26

| Component name | Composition 101 | Composition 102 | Composition 103 | Composition 104 | Composition 105 | Composition 106 |
|---|---|---|---|---|---|---|
| Betamethasone butylate propionate | 0.05 | 0.05 | 0.05 | 0.05 | 0.05 | 0.05 |
| N-methyl-2-pyrrolidone | 3 | 3 | 3 | 3 | 3 | 3 |
| 1,3-butylene glycol | 40 | 30 | 25 | 20 | 15 | 10 |
| Polyoxyethylene (9) lauryl ether | 1.5 | 1.5 | 1.5 | 1.5 | 1.5 | 1.5 |
| Polyethylene glycol monostearate (40 E.O.) | 0.5 | 0.5 | 0.5 | 0.5 | 1.5 | 0.5 |
| Polyoxyethylene (60) hydrogenated castor oil | 0.5 | 0.5 | 0.5 | 0.5 | 1.5 | 0.5 |
| Hydrogenated soybean lecithin | 0.01 | 0.01 | 0.01 | 0.01 | 0.01 | 0.01 |
| Sodium hydroxide | q.s. | q.s. | q.s. | q.s. | q.s. | q.s. |
| Disodium edetate | 0.4 | 0.4 | 0.4 | 0.4 | 0.4 | 0.4 |
| Water | q.s. | q.s. | q.s. | q.s. | q.s. | q.s. |
| Solubilization | Good | Good | Good | Good | Good | Good |
| Foam | Good | Good | Good | Good | Good | Good |

Sodium hydroxide was used to adjust the pH to weakly acidic, the remainder being water.

Example 27

The compositions for pump foamers according to the present invention and Comparative Example were produced according to the following formulation. That is, formulation components were each weighed, and heat-dissolved at 80° C., and then solubilized with stirring, and cooled with stirring to room temperature to obtain each composition and Comparative Example. The conditions (the presence or absence of clouding) of each composition were visually inspected immediately after preparation. Further, these compositions each packed in a pump foamer container were discharged onto glass slides, and foamability (foam volume) and foam quality (texture fineness of foam) were observed. The formulation components shown in the table are expressed in mass %. The results showed that the external compositions for pump foamers comprising an active ingredient were able to be manufactured using various phospholipids.

(Clouding)
No clouding observed by visual inspection (Good)
Clouding observed by visual inspection (Poor)
(Foamability)
Sufficient volume of foam obtained upon discharged (Good)
Only small volume of foam obtained upon discharged (Fair)
No foam obtained upon discharged (Poor)
(Foam Quality)
Foam with fine texture obtained upon discharged (Good)
Foam with rough texture obtained upon discharged (Fair)
No foam obtained upon discharged (Poor)

TABLE 27

Table 27

| | Composition 107 | Composition 108 | Composition 109 | Composition 110 | Composition 111 | Composition 112 |
|---|---|---|---|---|---|---|
| Betamethasone butylate propionate | 0.05 | 0.05 | 0.05 | 0.05 | 0.05 | 0.05 |
| Polyoxyethylene (10) oleyether | 1.5 | 1.5 | 1.5 | 1.5 | 1.5 | 1.5 |
| Polyethylene glycol monostearate (40 E.O.) | 0.5 | 0.5 | 0.5 | 0.5 | 0.5 | 0.5 |
| Polyoxyethylene (60) hydrogenated castor oil | 0.5 | 0.5 | 0.5 | 0.5 | 0.5 | 0.5 |
| N-methyl-2-pyrrolidone | 6 | 6 | 6 | 6 | 6 | 6 |
| 1,3-butylene glycol | 15 | 15 | 15 | 15 | 15 | 15 |
| Hydrogenated soybean lecithin | 0.01 | | | | 0.1 | |
| Soybean lecithin | | 0.01 | | | | |
| Hydroxylated soybean lecithin | | | 0.01 | | | |
| Ceramide | | | | 0.01 | | |
| Water | 76.44 | 76.44 | 76.44 | 76.44 | 76.35 | 76.45 |
| Clouding | Good | Good | Good | Good | Good | Good |
| Foamability | Good | Good | Good | Good | Good | Good |
| Foam quality | Good | Good | Good | Fair | Good | Fair |

Example 28

The compositions for pump foamers were prepared as in Example 3 according to the following formulations. Results are shown in Table 28. The compositions according to the present invention showed outstanding foaming capability.

TABLE 28

Table 28

| Formulation components | Composition 113 | Composition 114 |
|---|---|---|
| N-methyl-2-pyrrolidone | 6 | |
| N-ethyl-2-pyrrolidone | | 6 |
| Polyoxyethylene (9) lauryl ether | 1.5 | 1.5 |
| Polyethylene glycol monostearate (40 E.O.) | 0.5 | 0.5 |
| Polyoxyethylene (60) hydrogenated castor oil | 0.5 | 0.5 |
| 1,3-butylene glycol | 15 | 15 |
| Hydrogenated soybean lecithin | 0.01 | 0.01 |
| Water | 76.49 | 76.49 |
| Clouding | Good | Good |
| Foam height (mm) (immediately after stirring) | 41.13 | 42.50 |
| Foam quality (texture fineness) | Good | Good |

Example 29

Preparation was performed as in Example 9 according to the following formulations, and evaluation was then performed. Results are shown in Table 29. The results showed that a solubilized state was able to be obtained, and the external compositions for pump foamers having excellent foamability were able to be manufactured when certain solvents were included.

TABLE 29

Table 29

| Formulation components | Composition 115 | Composition 116 | Composition 117 | Composition 118 | Composition 119 |
|---|---|---|---|---|---|
| Betamethasone butylate propionate | 0.05 | 0.05 | 0.05 | 0.05 | 0.05 |
| N-methyl-2-pyrrolidone | 6 | | | | |
| Benzyl alcohol | | 6 | | | |
| Propylene carbonate | | | 6 | | |
| Crotamiton | | | | 6 | |
| Polyoxyethylene (9) lauryl ether | 1.5 | 1.5 | 1.5 | 1.5 | 1.5 |

TABLE 29-continued

Table 29

| Formulation components | Composition 115 | Composition 116 | Composition 117 | Composition 118 | Composition 119 |
|---|---|---|---|---|---|
| Polyethylene glycol monostearate (40 E.O.) | 1.5 | 1.5 | 1.5 | 1.5 | 1.5 |
| Polyoxyethylene (60) hydrogenated castor oil | 1.5 | 1.5 | 1.5 | 1.5 | 1.5 |
| 1,3-butylene glycol | 15 | 15 | 15 | 15 | 15 |
| Polyethylene glycol 400 | 2.5 | 2.5 | 2.5 | 2.5 | 2.5 |
| D-sorbitol | 0.25 | 0.25 | 0.25 | 0.25 | 0.25 |
| Water | 71.7 | 71.7 | 71.7 | 71.7 | 77.7 |
| Solubilization | Good | Good | Good | Poor | Poor |
| Foam | Good | Good | Good | Poor | Fair |

Example 30

The composition having the following formulation was prepared as in Example 9, and then evaluated. The results showed that a formulation broadly having excellent foamability and foam quality was able to be obtained when N-alkyl 2-pyrrolidone was used as a solvent.

TABLE 30

Table 30

| Formulation components | Composition 120 |
|---|---|
| N-methyl-2-pyrrolidone | 6 |
| Polyoxyethylene (20) oleylether | 1.5 |
| Polyethylene glycol monostearate (40 E.O.) | 0.5 |
| Polyoxyethylene (60) hydrogenated castor oil | 0.5 |
| 1,3-butylene glycol | 15 |
| Hydrogenated soybean lecithin | 0.01 |
| Water | 76.49 |
| Solubilization | Good |
| Foam | Good |

Example 31

Figure 13:
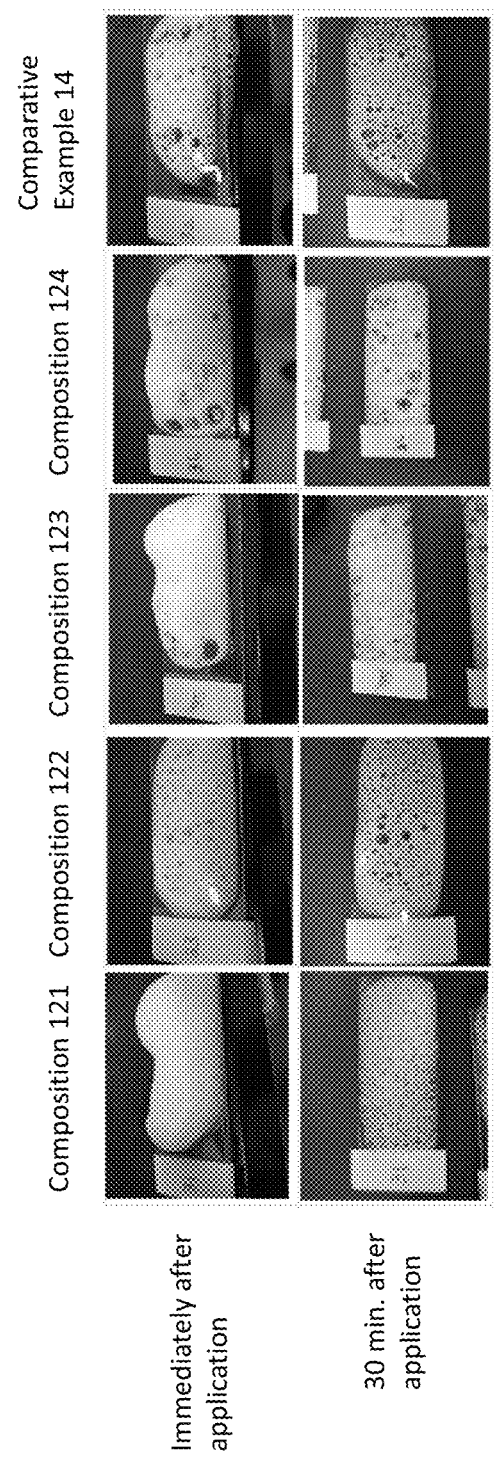
FIG. 13 shows images illustrating the results from Example 31.

Compositions were produced as in Example 1 according to the following formulations, and then evaluated. Results are shown in Table 31 and FIG. 13.

The results showed that each composition served as a composition for pump foamers having excellent foamability, foam quality, and persistency. The results also showed that polyoxyethylene alkyl or alkenyl ether served as an excellent nonionic surfactant in the compositions for the pump foamers according to the present invention.

Example 32

A composition was prepared according to the following formulation and the procedures used in Example 3, and then evaluated. Results are shown in Table 32. Each composition showed excellent foaming capability.

TABLE 32

Table 32

| Formulation components | Composition 125 |
|---|---|
| Betamethasone butyrate propionate | 0.05 |
| Polyoxyethylene (9) lauryl ether | 1.5 |
| Polyethylene glycol monostearate (40 E.O.) | 0.5 |
| Polyoxyethylene (60) hydrogenated castor oil | 0.5 |
| N-methyl-2-pyrrolidone | 6 |
| 1,3-butylene glycol | 15 |
| Hydrogenated soybean lecithin | 0.01 |
| Water | 76.44 |
| Clouding | Good |
| Foam height (mm) | 43.60 |
| Foam quality | Good |

Example 33

Figure 14:
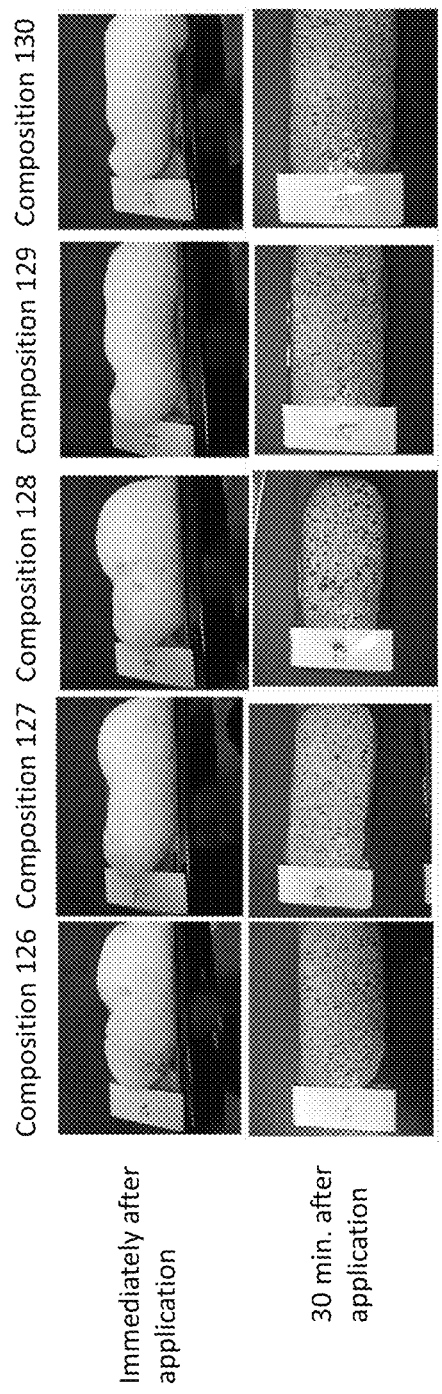
FIG. 14 shows images illustrating the results from Example 33.

Compositions were produced as in Example 3 according to the following formulations, and then evaluated in a similar manner. Results are shown in Table 33 and FIG. 14. The results showed that each composition served as a composition for pump foamers capable of solubilizing a poorly soluble drug and having excellent foamability, foam quality, and persistency.

TABLE 31

Table 31

| Formulation components | Composition 121 | Composition 122 | Composition 123 | Composition 124 | Comparative Example 14 |
|---|---|---|---|---|---|
| Betamethasone butyrate propionate | 0.05 | 0.05 | 0.05 | 0.05 | 0.05 |
| Polyoxyethylene (10) oleylether | 7 | | 1.5 | 3.5 | |
| Polyethylene glycol monostearate (10 E.O.) | | | | 3.5 | 7 |
| Polyoxyethylene (60) hydrogenated castor oil | | 7 | 5.5 | | |
| N-methyl-2-pyrrolidone | 5 | 5 | 5 | 5 | 5 |
| Diisopropyl adipate | 1 | 1 | 1 | 1 | 1 |
| Ethanol | 10 | 10 | 10 | 10 | 10 |
| Polyethylene glycol 400 | 25 | 25 | 25 | 25 | 25 |
| Glycerin | 5 | 5 | 5 | 5 | 5 |
| Water | 46.95 | 46.95 | 46.95 | 46.95 | 46.95 |
| State of composition (presence of clouding) | Good | Good | Good | Good | Good |
| State of composition (presence of separation) | Good | Good | Good | Good | Poor |
| Foamability immediately after discharged (foam volume) | Good | Good | Good | Good | Fair |
| Foam quality immediately after discharged | Good | Fair | Good | Good | Poor |
| Foam volume 30 minutes after discharged | Fair | Fair | Good | Good | Fair |
| Foam quality 30 minutes after discharged | Good | Fair | Good | Good | Poor |

TABLE 33

Table 33

| Formulation components | Composition 126 | Composition 127 | Composition 128 | Composition 129 | Composition 130 |
|---|---|---|---|---|---|
| Betamethasone butyrate propionate | 0.05 | 0.05 | 0.05 | 0.05 | 0.05 |
| Polyoxyethylene oleyl (10) ether | 1.5 | 1.5 | 1.5 | 1.5 | 1.5 |
| Polyethylene glycol monostearate (10 E.O.) | 3.5 | 3.5 | 3.5 | 3.5 | 3.5 |
| Polyoxyethylene (60) hydrogenated castor oil | 2 | 2 | 2 | 2 | 2 |
| N-methyl-2-pyrrolidone | 5 | 5 | 5 | 5 | 5 |
| Diisopropyl adipate | 1 | 1 | 1 | 1 | 1 |
| Ethanol | 10 | | | | |
| 1,3-butylene glycol | | 10 | | | |
| Polyethylene glycol 400 | | | 10 | | |
| Glycerin | | | | 10 | |
| Propylene glycol | | | | | 10 |
| Water | 76.95 | 76.95 | 76.95 | 76.95 | 76.95 |
| State of composition (presence of clouding) | Good | Good | Good | Good | Good |
| State of composition (presence of separation) | Good | Good | Good | Good | Good |
| Foamability immediately after discharged (foam volume) | Good | Good | Good | Good | Good |
| Foam quality immediately after discharged | Good | Good | Good | Good | Good |
| Foam volume 30 minutes after discharged | Good | Good | Good | Good | Good |
| Foam quality 30 minutes after discharged | Fair | Fair | Fair | Fair | Fair |

Example 34

Compositions were prepared as in Example 3 according to the following formulations, and then evaluated in a similar manner. Results are shown in Table 34 and FIG. 15. Each composition showed excellent foaming capability. Note that crystals were precipitated when N-alkyl 2-pyrrolidone was replaced by diisopropyl adipate.

TABLE 34

Table 34

| Formulation components | Composition 131 | Composition 132 | Composition 133 |
|---|---|---|---|
| Betamethasone butyrate propionate | 0.05 | | |
| N-methyl-2-pyrrolidone | 6 | 6 | |
| N-ethyl-2-pyrrolidone | | | 6 |
| Polyoxyethylene (9) lauryl ether | 1.5 | 1.5 | 1.5 |
| Polyethylene glycol monostearate (40 E.O.) | 0.5 | 0.5 | 0.5 |
| Polyoxyethylene (60) hydrogenated castor oil | 0.5 | 0.5 | 0.5 |
| 1,3-butylene glycol | 15 | 15 | 15 |
| Hydrogenated soybean lecithin | 0.01 | 0.01 | 0.01 |
| Water | 76.44 | 76.49 | 76.49 |
| Clouding | Good | Good | Good |
| Foam height (mm) (immediately after stirring) | 43.60 | 41.13 | 42.50 |
| Foam quality (texture fineness) | Good | Good | Good |

Example 35

An external skin preparation was similarly produced according to the following formulation. This composition showed no clouding and good foamability.

TABLE 35

Table 35

| Formulation components | Composition 134 |
|---|---|
| Betamethasone butyrate propironate | 0.05 |
| Polyoxyethylene (9) lauryl ether | 1.5 |
| Polyethylene glycol monostearate (40 E.O.) | 0.5 |
| Polyoxyethylene (60) hydrogenated castor oil | 0.5 |
| N-methyl-2-pyrrolidone | 6 |
| 1,3-butylene glycol | 15 |
| Aqueous sodium hydroxide | q.s. |
| Disodium edetate | 0.2 |
| Water | q.s. |

Sodium hydroxide was used to adjust the pH to weakly acidic, the remainder being wat

Example 36

An external skin preparation was similarly produced according to the following formulation. This composition showed no clouding and good foamability.

TABLE 36

Table 36

| Formulation components | Composition 135 |
|---|---|
| Betamethasone butyrate propironate | 0.05 |
| Polyoxyethylene (9) lauryl ether | 1.5 |
| Polyethylene glycol monostearate (40 E.O.) | 0.5 |
| Polyoxyethylene (60) hydrogenated castor oil | 0.5 |
| N-methyl-2-pyrrolidone | 6 |
| 1,3-butylene glycol | 15 |
| Aqueous sodium hydroxide | q.s. |
| Hydrogenated soybean lecithin | 0.01 |
| Disodium edetate | 0.2 |
| Water | q.s. |

Sodium hydroxide was used to adjust the pH to weakly acidic, the remainder being wat

INDUSTRIAL APPLICABILITY

The present invention can be used in pharmaceutical products.

The invention claimed is:
1. An external composition that foams with a structure of a screen foamer, comprising;
   from 0.001 to 10 mass % of a lipophilic active ingredient;
   from 1 to 15 mass % of a nonionic surfactant in total as a foaming component; and
   from 12 to 45 mass % of polyhydric alcohol in total,
   wherein the external composition is a formulation free from liquefied gas,
   the nonionic surfactant is at least one surfactant selected from the group A consisting of polyoxyethylene alkyl ether, polyoxyethylene alkenyl ether, polyoxyethylene hydrogenated castor oil, polyoxyethylene fatty acid ester, polyoxyethylene sorbitan fatty acid ester, polyoxyethylene fatty acid glyceryl, polyoxypropylene polyoxyethylene alkyl ether, and polyoxypropylene polyoxyethylene alkenyl ether, and
   the polyhydric alcohol is at least one alcohol selected from the group B consisting of propylene glycol, dipropylene glycol, glycerin, diglycerin, 1,3-butylene glycol, 1,2-pentanediol, 1,2-hexanediol, polyethylene glycol, and polypropylene glycol.
2. The external composition according to claim 1, which is in a solubilized state before foaming.

3. The external composition according to claim 1, wherein the external composition further comprises an ionic surfactant in an amount in a range of 1 mass % or less in total.

4. An external skin preparation comprising the external composition according to claim 1, wherein the preparation is designed for foam of the external composition to stay at an application site.

5. The external composition according to claim 1, which is an aqueous system.

6. The external composition according to claim 1, wherein the nonionic surfactant has an HLB value in a range of 9 or more.

7. The external composition according to claim 1, wherein the external composition comprises the at least one nonionic surfactant selected from the group A in an amount in a range of 80 mass % or more of a total amount of nonionic surfactant contained in the external composition.

8. The external composition according to claim 1, wherein a carbon chain of a hydrophobic group in the nonionic surfactant of the group A has a carbon number in a range of 8 or more.

9. The external composition according to claim 1, comprising from 15 to 40 mass % of the polyhydric alcohol in total.

10. The external composition according to claim 1, further comprising phospholipid.

11. The external composition according to claim 1, further comprising from 1 to 40 mass % of at least one solvent selected from the group consisting of N-alkyl pyrrolidone, alkylene carbonate, benzyl alcohol, adipic acid diester, and sebacic acid diester.

12. An external composition, comprising:
   from 1 to 15 mass % of a nonionic surfactant in total, which is at least one surfactant selected from the group A consisting of polyoxyethylene alkyl ether, polyoxyethylene alkenyl ether, polyoxyethylene hydrogenated castor oil, polyoxyethylene fatty acid ester, polyoxyethylene sorbitan fatty acid ester, polyoxyethylene fatty acid glyceryl, polyoxypropylene polyoxyethylene alkyl ether, and polyoxypropylene polyoxyethylene alkenyl ether;
   from 0.001 to 10 mass % of a lipophilic active ingredient, which is at least one active ingredient selected from the group consisting of a steroid, a non-steroidal antiinflammatory agent, a microbicide, an antifungal agent, an antibiotic, an anti-itching agent, vitamin A, vitamin B, vitamin C, vitamin D, vitamin E, and an immunosuppressive agent, a mucopolysaccharide, and a heparinoid; and
   from 12 to 45 mass % of polyhydric alcohol in total, which is at least one alcohol selected from the group B consisting of propylene glycol, dipropylene glycol, glycerin, diglycerin, 1,3-butylene glycol, 1,2-pentanediol, 1,2-hexanediol, polyethylene glycol, and polypropylene glycol,
   wherein the external composition is a formulation free from liquefied gas, and
   the external composition is in a solubilized state before foaming.

13. An external skin preparation, comprising the external composition according to claim 1 packed in a container having the structure of the screen foamer.

14. A method of designing an aqueous external composition that foams with a structure of a screen foamer, comprising:
   selecting at least one nonionic surfactant from the group A consisting of polyoxyethylene alkyl ether, polyoxyethylene alkenyl ether, polyoxyethylene hydrogenated castor oil, polyoxyethylene fatty acid ester, polyoxyethylene sorbitan fatty acid ester, polyoxyethylene fatty acid glyceryl, polyoxypropylene polyoxyethylene alkyl ether, and polyoxypropylene polyoxyethylene alkenyl ether, wherein an amount of the at least one nonionic surfactant in the external composition is in a range from 1 to 15 mass % in total; and
   selecting at least one polyhydric alcohol from the group B consisting of propylene glycol, dipropylene glycol, glycerin, diglycerin, 1,3-butylene glycol, 1,2-pentanediol, 1,2-hexanediol, polyethylene glycol, and polypropylene glycol, wherein an amount of the at least one polyhydric alcohol in the external composition is in a range from 12 to 45 mass % in total,
   so that the composition that is prepared by heating and cooling constituent components comprising the at least one nonionic surfactant and the at least one polyhydric alcohol, with stirring is in a solubilized state,
   wherein the external composition is a formulation free from liquefied gas, and
   the external composition comprises a lipophilic active ingredient in a range from 0.001 to 10 mass %; the nonionic surfactant; and the polyhydric alcohol.

* * * * *